United States Patent
Xu et al.

(10) Patent No.: US 11,080,901 B2
(45) Date of Patent: *Aug. 3, 2021

(54) IMAGE QUALITY IMPROVEMENT IN CONE BEAM COMPUTED TOMOGRAPHY IMAGES USING DEEP CONVOLUTIONAL NEURAL NETWORKS

(71) Applicant: Elekta, Inc., Atlanta, GA (US)

(72) Inventors: Jiaofeng Xu, Saint Louis, MO (US); Xiao Han, Chesterfield, MO (US)

(73) Assignee: Elekta, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/739,951

(22) Filed: Jan. 10, 2020

(65) Prior Publication Data
US 2020/0151922 A1    May 14, 2020

(51) Int. Cl.
*G06K 9/00* (2006.01)
*G06T 11/00* (2006.01)
(Continued)

(52) U.S. Cl.
CPC ............ *G06T 11/008* (2013.01); *A61B 6/032* (2013.01); *A61B 6/4085* (2013.01);
(Continued)

(58) Field of Classification Search
CPC ..... A61B 6/032; A61B 6/4085; A61B 6/5282; A61B 6/563; G06K 9/66; G06N 3/08;
(Continued)

(56) References Cited

U.S. PATENT DOCUMENTS

| | | |
|---|---|---|
| 10,573,032 B2 | 2/2020 | Xu et al. |
| 2013/0051519 A1 | 2/2013 | Yang et al. |

(Continued)

FOREIGN PATENT DOCUMENTS

| | | |
|---|---|---|
| CN | 111684492 | 9/2020 |
| CN | 112204620 | 1/2021 |

(Continued)

OTHER PUBLICATIONS

U.S. Appl. No. 15/564,983, filed Apr. 27, 2018, Image Quality in Cone Beam Computed Tomography Images Using Deep Convolutional Neural Networks.

(Continued)

*Primary Examiner* — Xin Jia
(74) *Attorney, Agent, or Firm* — Schwegman Lundberg & Woessner, P.A.; Sanjay Agrawal

(57) ABSTRACT

Systems and methods include training a deep convolutional neural network (DCNN) to reduce one or more artifacts using a projection space or an image space approach. In a projection space approach, a method can include collecting at least one artifact contaminated cone beam computed tomography (CBCT) projection space image, and at least one corresponding artifact reduced, CBCT projection space image from each patient in a group of patients, and using the artifact contaminated and artifact reduced CBCT projection space images to train a DCNN to reduce artifacts in a projection space image. In an image space approach, a method can include collecting a plurality of CBCT patient anatomical images and corresponding registered computed tomography anatomical images from a group of patients, and using the plurality of CBCT anatomical images and corresponding artifact reduced computed tomography anatomical images to train a DCNN to remove artifacts from a CBCT anatomical image.

23 Claims, 18 Drawing Sheets

(51) Int. Cl.
     *A61B 6/03*    (2006.01)
     *A61B 6/00*    (2006.01)
     *G06K 9/66*    (2006.01)
     *G06N 3/08*    (2006.01)
     *G06T 5/00*    (2006.01)

(52) U.S. Cl.
     CPC ............ *A61B 6/5282* (2013.01); *A61B 6/563* (2013.01); *G06K 9/66* (2013.01); *G06N 3/08* (2013.01); *G06T 5/005* (2013.01); *G06T 11/005* (2013.01); *G06T 2207/20084* (2013.01); *G06T 2210/41* (2013.01); *G06T 2211/424* (2013.01)

(58) Field of Classification Search
     CPC ................. G06T 11/005; G06T 11/008; G06T 2207/20084; G06T 2210/41; G06T 2211/424; G06T 5/005
     See application file for complete search history.

(56) References Cited

U.S. PATENT DOCUMENTS

| | | | |
|---|---|---|---|
| 2013/0070991 A1* | 3/2013 | Yang | G06K 9/00389 382/131 |
| 2013/0243298 A1* | 9/2013 | Bredno | G06T 11/008 382/131 |
| 2015/0201895 A1 | 7/2015 | Suzuki | |
| 2015/0213633 A1 | 7/2015 | Chang et al. | |
| 2016/0048972 A1 | 2/2016 | Kam et al. | |
| 2016/0114192 A1 | 4/2016 | Lachaine et al. | |
| 2017/0196529 A1* | 7/2017 | Lin | A61B 6/541 |
| 2018/0070902 A1* | 3/2018 | Lin | A61B 5/1077 |
| 2018/0374245 A1 | 12/2018 | Xu et al. | |
| 2019/0259493 A1 | 8/2019 | Xu et al. | |
| 2019/0304157 A1 | 10/2019 | Amer et al. | |
| 2019/0318474 A1 | 10/2019 | Han | |
| 2019/0333219 A1 | 10/2019 | Xu et al. | |

FOREIGN PATENT DOCUMENTS

| | | |
|---|---|---|
| JP | H08153194 | 6/1996 |
| WO | 2019005180 | 1/2019 |
| WO | 2019199699 | 10/2019 |
| WO | 2019209820 | 10/2019 |

OTHER PUBLICATIONS

U.S. Appl. No. 16/044,245, filed Jul. 24, 2018, Cone-Beam CT Image Enhancement Using Generative Adversarial Networks.
"International Application Serial No. PCT US2017 043479, International Search Report dated Nov. 21, 2017", 3 pgs.
"International Application Serial No. PCT US2017 043479, Written Opinion dated Nov. 21, 2017", 6 pgs.
"International Application Serial No. PCT US2019 026400, International Search Report dated Jun. 14, 2019", 4 pgs.
"International Application Serial No. PCT US2019 026400, Written Opinion dated Jun. 14, 2019", 8 pgs.
"International Application Serial No. PCT US2019 028710, International Search Report dated Aug. 22, 2019", 4 pgs.
"International Application Serial No. PCT US2019 028710, Written Opinion dated Aug. 22, 2019", 5 pgs.
"U.S. Appl. No. 15/964,983, Notice of Allowance dated Nov. 7, 2019", 20 pgs.
"U.S. Appl. No. 15/952,686, Non Final Office Action dated Dec. 12, 2019", 19 pgs.
"International Application Serial No. PCT US2017 043479, International Preliminary Report on Patentability dated Jan. 9, 2020", 8 pgs.
"U.S. Appl. No. 15/964,983, Corrected Notice of Allowability dated Jan. 15, 2020", 3 pgs.
"U.S. Appl. No. 15/964,983, Corrected Notice of Allowability dated Jan. 17, 2020", 16 pgs.
Chartsias, Agisilaos, "Adversarial Image Synthesis for Unpaired Multi-modal Cardiac Data", Image Analysis and Recognition : 11th International Conference, ICIAR 2014, Vilamoura, Portugal, (Sep. 26, 2017), 1-11.
Dong, Nie, "Medical Image Synthesis with Context-Aware Generative Adversarial Networks", Arxiv.Org, Cornell University Library, 201 Olin Library Cornell University Ithaca, Ny 14853, (Dec. 16, 2016), 12 pgs.
Gauthier, Jon, "Conditional generative adversarial nets for convolutional face generation", Class Project for Stanford CS231N: Convolutional Neural Networks for Visual Recognition, Winter semester 2014.5, (2014), 9 pgs.
Isola, Phillip, "Image-to-Image Translation with Conditional Adversarial Networks", arXiv:1611.07004 [cs.CV], (Nov. 22, 2017), 17 pgs.
Jin, Kyong, "Deep Convolutional Neural Network for Inverse Problems in Imagin", IEEE Transactions on Image Processing Publication of the IEEE Signal Processing Society, (Jun. 15, 2017), 4509-4522.
Matteo, Maspero, "Fast synthetic CT generation with deep learning for general pelvis MR-only Radiotherapy", Arxiv.Org, Cornell University Library, 201 Olin Library Cornell University Ithaca, NY 14853, (Feb. 19, 2018), 14 pgs.
Nie, Dong, "Estimating CT Image from MRI Data Using 3D Fully Convolutional Networks", (Sep. 27, 2016), 9 pgs.
Qingsong, Yang, "CT Image Denoising with Perceptive Deep Neural Networks", Arxiv.Org Cornell University Library 201 Olin Library Cornell University Ithaca NY, (Feb. 22, 2017), 8 pgs.
Schulze, R, "Artefacts in CBCT: a review", Dentomaxillofacial Radiology, (2011), 265-273.
Schulze, R, "Artefacts in CBCT: a review", The British Institute of Radiology 40, [Online] Retrieved from the internet: http: dmfr.birjournals.org, (2011), 265-273.
Schulze, Ralf Kurt Willy, "On cone-beam computed tomography artifacts induced by titanium implants", Clinical Oral Implants Research Clin. Oral Impl. Res. 21, (2010), 100-107.
Wojciech, Zbijewski, "Efficient Monte Carlo Based Scatter Artifact Reduction in Cone-Beam Micro-CT", IEEE, vol. 25, No. 7, (Jul. 7, 2006), 11 pgs.
Wolterink, Jelmer M., "Deep MR to CT Synthesis using Unpaired Data", International Conference on Computer Analysis of Images and Patterns. Caip 2017: Computer Analysis of Images and Patterns; [LECTURE Notes in Computer Science; Lect.Notes Computer], Springer, Berlin, Heidelberg, (Aug. 3, 2017), 10 pgs.
Wurfl, Tobias, "Deep Learning Computed Tomography", Network and Parallel Computing Notes in Computer Science Lect.Notes Computer Springer International Publishing CHAM, (Oct. 2, 2016), 432-440.
Zhu, Jun-Yan, "Unpaired Image-to-Image Translation using Cycle-Consistent Adversarial Networks", [Online], Retrieved from the Internet: URL: https: junyanz.github.io CycleGAN , (Accessed Mar. 1, 2018), 8 pgs.
Zhu, Jun-Yan, "Unpaired Image-to-Image Translation using Cycle-Consistent Adversarial Networks", Berkeley AI Research Lab, UC Berkeley; arXiv:1703.10593v4 [cs.CV], (Feb. 19, 2018), 20 pgs.
"Australian Application Serial No. 2017420781, Response filed 11-24-40 to First Examination Report dated Aug. 19, 2020", 32 pgs.
"European Application Serial No. 17746342.9, Response filed Jan. 27, 2021 to Communication Pursuant to Article 94(3) EPC dated Oct. 29, 2020", 16 pgs.
"Japanese Application Serial No. 2019-572231, Notification of Reasons for Refusal dated Feb. 9, 2021", w English Translation, 8 pgs.
"Australian Application Serial No. 2017420781, First Examination Report dated Aug. 19, 2020", 4 pgs.
"European Application Serial No. 17746342.9, Response to Communication pursuant to Rules 161(1) and 162 EPC, response filed Aug. 24, 2020", 12 pgs.
"European Application Serial No. 17746342.9, Communication Pursuant to Article 94(3) EPC dated Oct. 29, 2020", 6 pgs.

(56) References Cited

OTHER PUBLICATIONS

"International Application Serial No. PCT US2019 028710, International Preliminary Report on Patentability dated Nov. 5, 2020", 7 pgs.

"European Application Serial No. 17746342.9, Communication Pursuant to Article 94(3) EPC dated Mar. 26, 2021", 5 pgs.

"Japanese Application Serial No. 2019-572231, Response filed Mar. 15, 2021 to Notification of Reasons for Refusal dated Feb. 9, 2021", w/ English claims, 10 pgs.

"European Application Serial No. 19727531.6, Response to Communication pursuant to Rules 161(1) and 162 EPC filed May 14, 2021", 25 pgs.

* cited by examiner

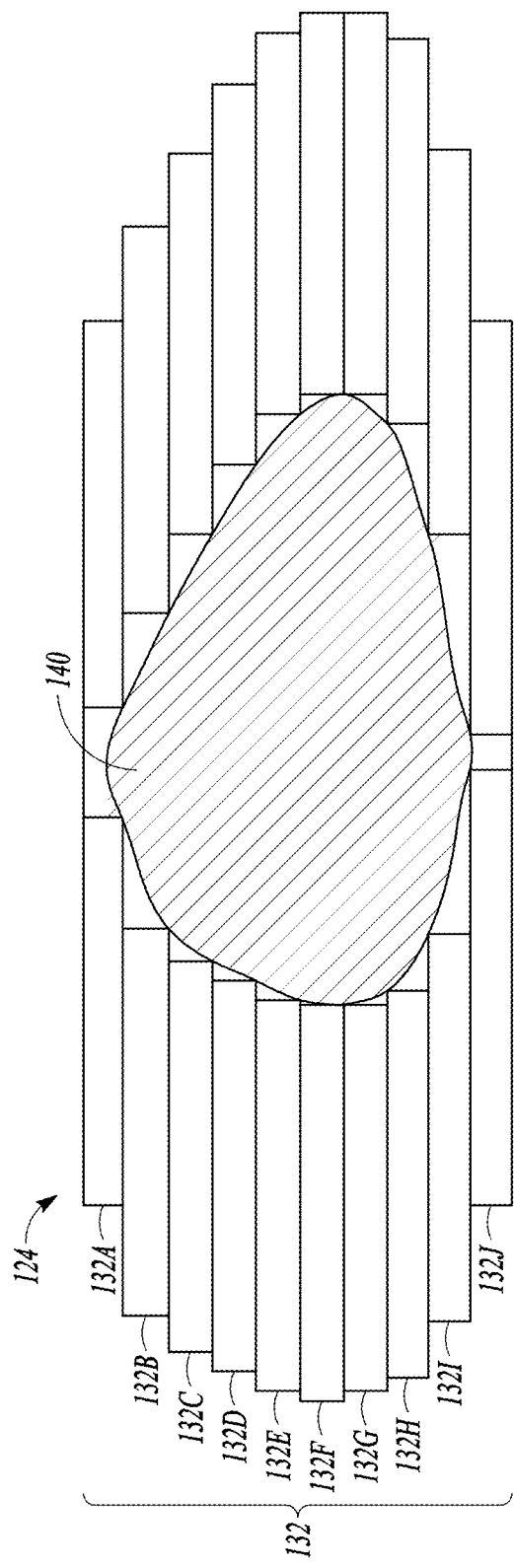

IMAGE QUALITY IMPROVEMENT IN CONE BEAM COMPUTED TOMOGRAPHY IMAGES USING DEEP CONVOLUTIONAL NEURAL NETWORKS

CROSS REFERENCE TO RELATED APPLICATIONS

This application is a continuation of and claims the benefit of priority of U.S. application Ser. No. 15/964,983, filed Apr. 27, 2018, which claims the benefit of priority from U.S. Provisional Patent Application No. 62/524,933 filed on Jun. 26, 2017, each of which are incorporated by reference in their entireties.

TECHNICAL FIELD

Embodiments of the present invention pertain generally to improving image quality in a cone beam computed tomography image. In particular, the present invention pertains to using deep learning technologies to reduce artifacts in a cone beam computed tomography image.

OVERVIEW

Radiation therapy has been utilized to treat cancers and other ailments in mammalian (e.g., human and animal) tissue. X-ray cone beam computed tomography (CBCT) has been widely employed in modern radiation therapy for patient setup and adaptive re-planning. CBCT has also been employed for diagnostic purposes, such as dental imaging and planning of implants, to name only a few. Moreover, X-ray CBCT has been increasingly employed in many imaging related applications, such as micro-computed tomography. X-ray CBCT can include relatively simple geometric configuration with a circular scanning geometry. The setup for CBCT can also be easily integrated with other imaging modalities for various purposes.

However, the image quality of CBCT images has been a source of complaints by medical physicists, doctors and other researchers. In general, CBCT images can contain many different types of artifacts (including all types of noise). An image artifact can be defined as a structure in reconstructed data that is not present in the real object under investigation. Generally speaking, artifacts can be induced by discrepancies between the actual measured data under the specific physical conditions (such as the physical parameters of a CBCT scanner and compositions and characteristics of the object undergoing scanning) and the implied mathematical assumptions used for 2D/3D image reconstruction.

The artifacts and noise in CBCT images can seriously hinder adaptive replanning, affect a doctor's diagnosis and make many other image processing steps impossible or difficult, such as image segmentation. Since each artifact can be caused by one or more different factors, different methods can be employed to suppress each different artifact. Because of this, it can be very time-consuming and very complicated, and sometimes impossible to suppress all artifacts, or even some of them by employing traditional methods. Although researchers have done many investigations and developed several related methods for the purpose of reducing artifacts in CBCT images, currently, there is not any existing simple and efficient method which can suppress all general artifacts. Therefore, there exists a significant need to develop a novel, efficient and simple method to suppress artifacts and noise in CBCT images.

In an aspect, the disclosure can feature a method for training a deep convolutional neural network, such as to reduce one or more artifacts in at least one projection space image. The method can include collecting at least one artifact contaminated cone beam computed tomography projection space image, and at least one corresponding artifact reduced, cone beam computed tomography projection space image from each patient in a group of patients. The method can also include using the at least one artifact contaminated cone beam computed tomography projection space image and the at least one corresponding artifact reduced, cone beam computed tomography projection space image collected from each patient in the group of patients to train a deep convolutional neural network, such as to reduce one or more artifacts in a projection space image. The method can also include collecting a plurality of pairs of projection space images from each patient in a group of patients, wherein an individual pair of projection space images can include an artifact contaminated cone beam computed tomography projection space image and a corresponding artifact reduced cone beam computed tomography projection space image. The method can also include using the plurality of pairs of projection space images collected from each patient in the group of patients to train a deep convolutional neural network for regression, such as to reduce one or more artifacts in the projection space image. The method can also include collecting a plurality of view-adjacent, artifact contaminated cone beam computed tomography projection space images, and a corresponding artifact reduced, central one of the plurality of view-adjacent cone beam computed tomography projection space images from each patient in a group of patients and using the plurality of view-adjacent, artifact contaminated cone beam computed tomography projection space images and the corresponding artifact reduced, central one of the plurality of view-adjacent cone beam computed tomography projection space images collected from each patient in the group of patients to train a deep convolutional neural network, such as to reduce one or more artifacts in at least a central one of a plurality of view-adjacent, cone beam computed tomography projection space images. The method can also include collecting a three-dimensional, artifact contaminated cone beam computed tomography projection volume, and a corresponding artifact reduced, cone beam computed tomography projection volume from each patient in a group of patients, and using the three-dimensional, artifact contaminated cone beam computed tomography projection volume, and the corresponding artifact reduced, cone beam computed tomography projection volume collected from each patient in the group of patients to train a deep convolutional neural network, such as to reduce one or more artifacts in the cone beam computed tomography projection volume.

In an aspect, the disclosure can feature a method of using a deep convolutional neural network to reduce one or more artifacts in a projection space image collected from a patient. The method can include collecting at least one artifact contaminated projection space image from the patient. The method can also include using a trained deep convolutional neural network, such as to reduce one or more artifacts in the at least one projection space image collected from the patient, the deep convolutional neural network can include a model trained, such as by using a collected plurality of projection space images from a group of patients. The trained deep convolutional neural network can reduce at least one artifact in a projection space image collected from the patient in near real-time, wherein the at least one artifact can include at least one of a scattering artifact or a noise artifact. The method can also include collecting an artifact contaminated cone beam computed tomography projection space image from the patient and using a trained deep convolutional neural network, such as to reduce one or more artifacts in the cone beam tomography projection space image collected from the patient, the deep convolutional neural network can include a model trained, such as by using a collected plurality of pairs of projection space images from each patient in a group of patients, wherein an individual pair of projection space images can include an artifact contaminated cone beam computed tomography projection space image and a corresponding artifact reduced cone beam computed tomography projection space image. The method can also include collecting a plurality of view-adjacent, artifact contaminated cone beam computed tomography projection space images from the patient and using a trained deep convolutional neural network, such as to reduce one or more artifacts in a central one of the plurality of view-adjacent, cone beam computed tomography projection space images collected from the patient, the deep convolutional neural network can include a model trained by using a collected plurality of view-adjacent, artifact contaminated cone beam computed tomography projection space images, and a corresponding artifact reduced, central one of the plurality of view-adjacent cone beam computed tomography projection space images from each patient in a group of patients. The trained deep convolutional neural network can use at least one correlation between the plurality of view-adjacent, artifact contaminated cone beam computed tomography projection space images collected from the patient, such as to reduce the one or more artifacts in the central one of the plurality of view-adjacent, cone beam computed tomography projection space images collected from the patient. The method can also include collecting a three-dimensional artifact contaminated cone beam computed tomography projection volume from the patient and using the trained deep convolutional neural network, such as to reduce one or more artifacts in the cone beam computed tomography projection volume collected from the patient, the deep convolutional neural network can include a model trained by using a collected three-dimensional, artifact contaminated cone beam computed tomography projection volume, and the corresponding artifact reduced, cone beam computed tomography projection volume collected from each patient in a group of patients.

In an aspect, the disclosure can feature a method for training a deep convolutional neural network to reduce one or more artifacts in a cone beam computed tomography anatomical image. The method can include collecting a plurality of cone beam computed tomography patient anatomical images and corresponding computed tomography anatomical images from a group of patients. The method can also include using the plurality of cone beam computed tomography anatomical images and corresponding artifact reduced computed tomography anatomical images to train a deep convolutional neural network for regression, such as to remove artifacts from a cone beam computed tomography anatomical image. The method can also include collecting a plurality of pairs of anatomical images from each patient in a group of patients, wherein an individual pair of anatomical images can include an artifact contaminated cone beam computed tomography anatomical image and a corresponding artifact reduced computed tomography anatomical image and using the collected images to train a deep convolutional neural network, such as to reduce one or more artifacts in a cone beam computed tomography anatomical image. The method can also include collecting a plurality of adjacent, artifact contaminated cone beam computed tomography anatomical images, and an artifact reduced computed tomography anatomical image corresponding to the central one of the plurality of adjacent artifact contaminated cone beam computed tomography anatomical images for each patient in a group of patients using the collected images to train a deep convolutional neural network, such as to reduce one or more artifacts in at least a central one of a plurality of cone beam computed tomography anatomical images. The method can also include collecting at least one artifact contaminated cone beam computed tomography anatomical volume, and at least one corresponding artifact reduced computed tomography anatomical volume for each patient in a group of patients and using the collected images to train a deep convolutional neural network, such as to reduce one or more artifacts in a cone beam computed tomography anatomical volume.

In an aspect, the disclosure can feature a method of using a deep convolutional neural network to reduce one or more artifacts in an anatomical image collected from a patient. The method can include collecting at least one artifact contaminated anatomical image from the patient. The method can also include using a trained deep convolutional neural network, such as to reduce one or more artifacts in the at least one anatomical image collected from the patient, the deep convolutional neural network can include a model trained by using a collected plurality of artifact contaminated anatomical images and corresponding artifact reduced anatomical images from a group of patients.

The trained deep convolutional neural network can reduce at least one artifact in an anatomical image collected from the patient in near real-time, wherein the at least one artifact can include at least one of a scattering artifact, a beam hardening artifact, a noise artifact, an extinction artifact, an exponential edge gradient artifact, an aliasing artifact, a ring artifact, a streaking artifact, or a motion artifact.

The method can also include collecting an artifact contaminated cone beam computed tomography anatomical image from the patient and using a trained deep convolutional neural network, such as to reduce one or more artifacts in the cone beam computed tomography anatomical image collected from the patient, the deep convolutional neural network can include a model trained by using a collected plurality of pairs of anatomical images from each patient in a group of patients, wherein an individual pair of anatomical images can include an artifact contaminated cone beam computed tomography anatomical image and a corresponding artifact reduced computed tomography anatomical image. The method can also include collecting a plurality of adjacent, artifact contaminated cone beam computed tomography anatomical images and using a trained deep convolutional neural network, such as to reduce one or more artifacts in a central one of the plurality of adjacent, cone beam computed tomography anatomical images collected from the patient, the deep convolutional neural network can include a model trained by using a collected plurality of adjacent, artifact contaminated cone beam computed tomography anatomical images, and an artifact reduced computed tomography anatomical image corresponding to the central one of the plurality of adjacent artifact contaminated cone beam computed tomography anatomical images for each patient in a group of patients. The method can also include collecting at least one, artifact contaminated cone beam computed tomography anatomical volume and using a trained deep convolutional neural network, such as to reduce one or more artifacts in the at least one cone beam computed tomography anatomical volume collected from the patient, the deep convolutional neural network can include a model trained by using a collected at least one artifact contaminated cone beam computed tomography anatomical volume, and at least one corresponding artifact reduced computed tomography anatomical volume for each patient in a group of patients.

In an aspect, the disclosure can feature a method for training a deep convolutional neural network to reduce one or more artifacts in a cone beam computed tomography anatomical image. The method can include collecting a plurality of cone beam computed tomography patient anatomical images and corresponding artifact reduced anatomical images from a group of patients. The method can also include using the plurality of cone beam computed tomography anatomical images and corresponding artifact reduced anatomical images to train a deep convolutional neural network, such as to remove artifacts from a cone beam computed tomography anatomical image. The method can also include using at least one of iterative algorithms, computer simulations, physical phantoms, or registered computed tomography anatomical images to provide the corresponding artifact reduced anatomical images from the group of patients.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIG. 5 illustrates an exemplary collimator configuration for shaping, directing, or modulating an intensity of a radiation therapy beam.

DETAILED DESCRIPTION

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

Figure 1:
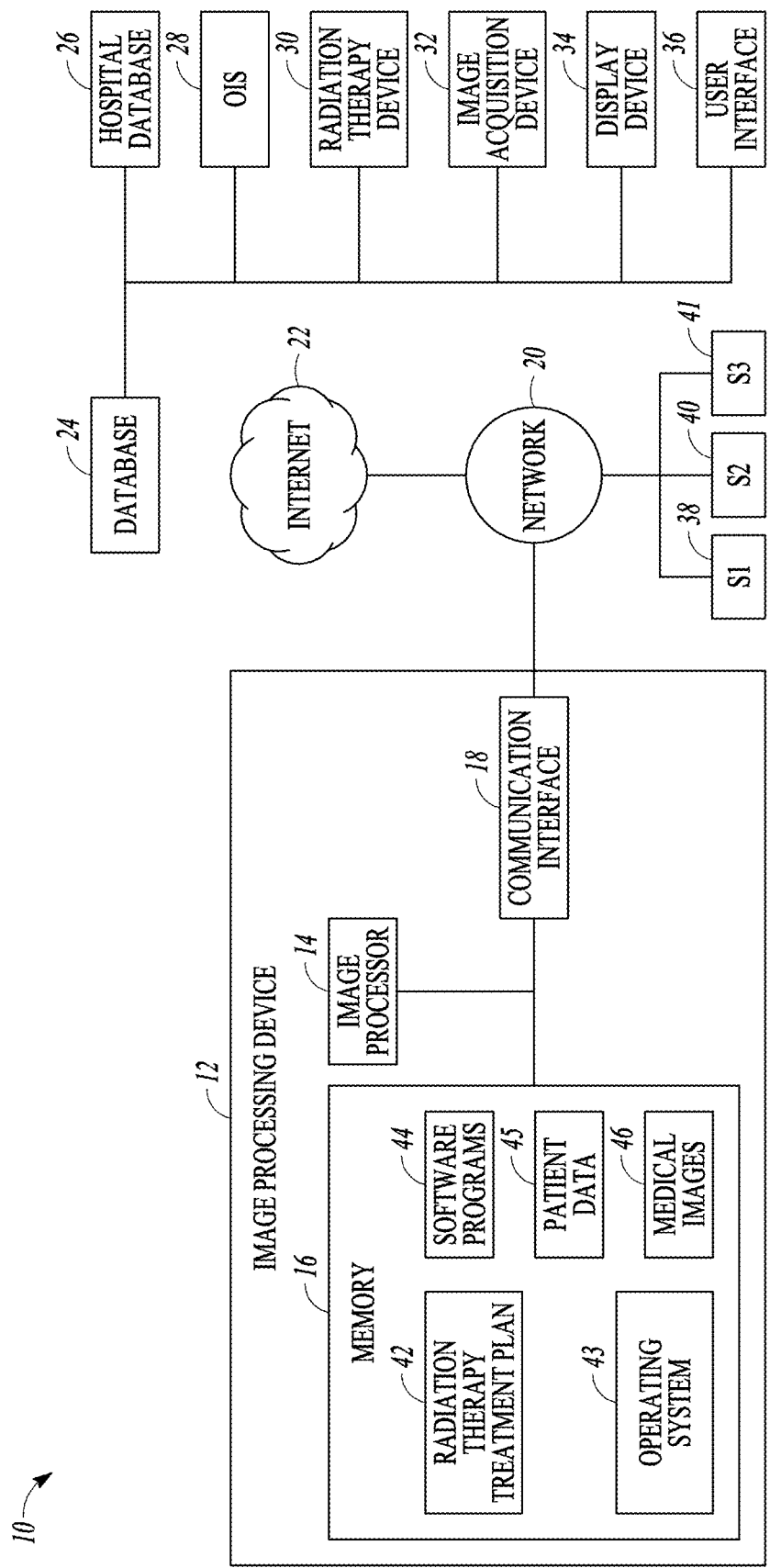
FIG. 1 illustrates an exemplary radiotherapy system, according to some embodiments of the present disclosure.

FIG. 1 illustrates an exemplary radiotherapy system 10 for providing radiation therapy to a patient. The radiotherapy system 10 includes an image processing device, 12. The image processing device 12 may be connected to a network 20. The network 20 may be connected to the Internet 22. The network 20 can connect the image processing device 12 with one or more of a database 24, a hospital database 26, an oncology information system (OIS) 28, a radiation therapy device 30, an image acquisition device 32, a display device 34, and a user interface 36. The image processing device 12 is configured to generate radiation therapy treatment plans 42 to be used by the radiation therapy device 30.

The image processing device 12 may include a memory device 16, a processor 14 and a communication interface 18. The memory device 16 may store computer-executable instructions, such as an operating system 43, a radiation therapy treatment plans 42 (e.g., original treatment plans, adapted treatment plans and the like), software programs 44 (e.g., artificial intelligence, deep learning, neural networks, radiotherapy treatment plan software), and any other computer-executable instructions to be executed by the processor 14. In an embodiment, the software programs 44 may convert medical images of one format (e.g., MRI) to another format (e.g., CT) by producing synthetic images, such as a pseudo-CT image. For instance, the software programs 44 may include image processing programs to train a predictive model for converting a medial image 46 in one modality (e.g., an MRI image) into a synthetic image of a different modality (e.g., a pseudo CT image); alternatively, the trained predictive model may convert a CT image into an MRI image. The memory device 16 may store data, including medical images 46, patient data 45, and other data required to create and implement a radiation therapy treatment plan 42.

In addition to the memory 16 storing the software programs 44, it is contemplated that software programs 44 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 44 when downloaded to image processing device 14 may be executed by image processor 14.

The processor 14 may be communicatively coupled to the memory device 16, and the processor 14 may be configured to execute computer executable instructions stored thereon. The processor 14 may send or receive medical images 46 to memory 16. For example, the processor 14 may receive medical images 46 from the image acquisition device 32 via the communication interface 18 and network 18 to be stored in memory 16. The processor 14 may also send medical images 46 stored in memory 16 via the communication interface 18 to the network 20 be either stored in database 24 or the hospital database 26.

Further, the processor 14 may utilize software programs 44 (e.g., a treatment planning software) along with the medical images 46 and patient data 45 to create the radiation therapy treatment plan 42. Medical images 46 may include information such as imaging data associated with a patient anatomical region, organ, or volume of interest segmentation data. Patient data 45 may include information such as (1) functional organ modeling data (e.g., serial versus parallel organs, appropriate dose response models, etc.); (2) radiation dosage data (e.g., dose-volume histogram (DVH) information; or (3) other clinical information about the patient and course of treatment (e.g., other surgeries, chemotherapy, previous radiotherapy, etc.).

In addition, the processor 14 may utilize software programs to generate intermediate data such as updated parameters to be used, for example, by a neural network model; or generate intermediate 2D or 3D image, which may then subsequently be stored in memory 16. The processor 14 may subsequently then transmit the executable radiation therapy treatment plan 42 via the communication interface 18 to the network 20 to the radiation therapy device 30, where the radiation therapy plan will be used to treat a patient with radiation. In addition, the processor 14 may execute software programs 44 to implement functions such as image conversion, image segmentation, deep learning, neural networks, and artificial intelligence. For instance, the processor 14 may execute software programs 44 that train or contour a medical image; such software 44 when executed may train a boundary detector, utilize a shape dictionary.

The processor 14 may be a processing device, include one or more general-purpose processing devices such as a microprocessor, a central processing unit (CPU), a graphics processing unit (GPU), an accelerated processing unit (APU), or the like. More particularly, the processor 14 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 14 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 14 may be a special-purpose processor, rather than a general-purpose processor. The processor 14 may include one or more known processing devices, such as a microprocessor from the Pentium™, Core™, Xeon™, or Itanium® family manufactured by Intel™, the Turion™, Athlon™, Sempron™, Opteron™ FX™, Phenom™ family manufactured by AMD™, or any of various processors manufactured by Sun Microsystems. The processor 14 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 14 may also include accelerated processing units such as the Desktop A-4(6,8) Series manufactured by AMD™, the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 14 can execute sequences of computer program instructions, stored in memory 16, to perform various operations, processes, methods that will be explained in greater detail below.

The memory device 16 can store medical images 46. In some embodiments, the medical images 46 may include one or more MRI image (e.g., 2D MRI, 3D MRI, 2D streaming MRI, 4D MRI, 4D volumetric MRI, 4D cine MRI, etc), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the medical images 46 may also include medical image data, for instance, training images, and ground truth images, contoured images. In an embodiment, the medical images 46 may be received from the image acquisition device 32. Accordingly, image acquisition device 32 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 46 may be received and stored in any type of data or any type of format that the image processing device 12 may use to perform operations consistent with the disclosed embodiments. The memory device 12 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 14, or any other type of computer device. The computer program instructions can be accessed by the processor 14, read from the ROM, or any other suitable memory location, and loaded into the RAM for execution by the processor 14. For example, the memory 16 may store one or more software applications. Software applications stored in the memory 16 may include, for example, an operating system 43 for common computer systems as well as for software-controlled devices. Further, the memory 16 may store an entire software application, or only a part of a software application, that are executable by the processor 14. For example, the memory device 16 may store one or more radiation therapy treatment plans 42.

The image processing device 12 can communicate with the network 20 via the communication interface 18, which is communicatively coupled to the processor 14 and the memory 16. The Communication interface 18 may provide communication connections between the image processing device 12 and radiotherapy system 10 components (e.g., permitting the exchange of data with external devices). For instance the communication interface 18 may in some embodiments have appropriate interfacing circuitry to connect to the user interface 36, which may be a hardware keyboard, a keypad, or a touch screen through which a user may input information into radiotherapy system 10.

Communication interface 18 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a Wi-Fi adaptor), a telecommunication adaptor (e.g., 3G, 4G/LTE and the like), and the like. Communication interface 18 may include one or more digital and/or analog communication devices that permit image processing device 12 to communicate with other machines and devices, such as remotely located components, via the network 20.

The network 20 may provide the functionality of a local area network (LAN), a wireless network, a cloud computing environment (e.g., software as a service, platform as a service, infrastructure as a service, etc.), a client-server, a wide area network (WAN), and the like. For example, network 20 may be a LAN or a WAN that may include other systems S1 (38), S2 (40), and S3 (41). Systems S1, S2, and S3 may be identical to image processing device 12 or may be different systems. In some embodiments, one or more of systems in network 20 may form a distributed computing/simulation environment that collaboratively performs the embodiments described herein. In some embodiments, one or more systems S1, S2, and S3 may include a CT scanner that obtain CT images (e.g., medical images 46). In addition, network 20 may be connected to internet 22 to communicate with servers and clients that reside remotely on the internet.

Therefore, network 20 can allow data transmission between the image processing device 12 and a number of various other systems and devices, such as the OIS 28, the radiation therapy device 30, and the image acquisition device 32. Further, data generated by the OIS 28 and/or the image acquisition device 32 may be stored in the memory 16, the database 24, and/or the hospital database 26. The data may be transmitted/received via network 20, through communication interface 18 in order to be accessed by the processor 14, as required.

The image processing device 12 may communicate with database 24 through network 20 to send/receive a plurality of various types of data stored on database 24. For example, database 24 may include machine data that is information associated with a radiation therapy device 30, image acquisition device 32, or other machines relevant to radiotherapy. Machine data information may include radiation beam size, arc placement, beam on and off time duration, control points, segments, multi-leaf collimator (MLC) configuration, gantry speed, MRI pulse sequence, and the like. Database 24 may be a storage device. One skilled in the art would appreciate that database 24 may include a plurality of devices located either in a central or a distributed manner.

In some embodiments, database 24 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 14 may communicate with database 24 to read images into memory 16 or store images from memory 16 to database 24. For example, the database 24 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) data, etc.) that the database 24 received from image acquisition device 32. Database 24 may store data to be used by the image processor 14 when executing software program 44, or when creating radiation therapy treatment plans 42. The image processing device 12 may receive the imaging data 46 (e.g., 2D MRI slice images, CT images, 2D Fluoroscopy images, X-ray images, 3DMRI images, 4D MRI images, etc.) either from the database 24, the radiation therapy device 30 (e.g., a MRI-Linac), and or the image acquisition device 32 to generate a treatment plan 42.

In an embodiment, the radiotherapy system 100 can include an image acquisition device 32 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 32 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 32 can be stored within database 24 as either imaging data and/or test data. By way of example, the images acquired by the imaging acquisition device 32 can be also stored by the image processing device 12, as medical image data 46 in memory 16.

In an embodiment, for example, the image acquisition device 32 may be integrated with the radiation therapy device 30 as a single apparatus (e.g., a MRI device combined with a linear accelerator, also referred to as an "MRI-Linac." Such an MRI-Linac can be used, for example, to determine a location of a target organ or a target tumor in the patient, so as to direct radiation therapy accurately according to the radiation therapy treatment plan 42 to a predetermined target.

The image acquisition device 32 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 32 can acquire a 2D slice in any orientation. For example, an orientation of the 2D slice can include a sagittal orientation, a coronal orientation, or an axial orientation. The processor 14 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 32 in "real-time" while a patient is undergoing radiation therapy treatment, for example, when using the radiation therapy device 30. "Real-time" meaning acquiring the data in at least milliseconds or less.

The image processing device 12 may generate and store radiation therapy treatment plans 42 for one or more patients. The radiation therapy treatment plans 42 may provide information about a particular radiation dose to be applied to each patient. The radiation therapy treatment plans 42 may also include other radiotherapy information, such as beam angles, dose-histogram-volume information, the number of radiation beams to be used during therapy, the dose per beam, and the like.

The image processor 14 may generate the radiation therapy treatment plan 42 by using software programs 44 such as treatment planning software, such as Monaco®, manufactured by Elekta AB of Stockholm, Sweden. In order to generate the radiation therapy treatment plans 42, the image processor 14 may communicate with the image acquisition device 32 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the treatment planning device 110 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 32 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan 42 that may be stored in memory 16 or database 24. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 12 can generate a tailored radiation therapy treatment plan 42 having these parameters in order for the radiation therapy device 30 to provide radiotherapy treatment to the patient.

In addition, the radiotherapy system 10 may include a display device 34 and a user interface 36. The display device 34 may include one or more display screens that display medical images, interface information, treatment planning parameters (e.g., contours, dosages, beam angles, etc.) treatment plans, a target, localizing a target and/or tracking a target, or any related information to the user. The user interface 36 may be a keyboard, a keypad, a touch screen or any type of device that a user may input information to radiotherapy system 10. Alternatively, the display device 34 and the user interface 36 may be integrated into a device such as a tablet computer, e.g., Apple iPad®, Lenovo Thinkpad®, Samsung Galaxy®, etc.

Furthermore, any and all components of the radiotherapy system 10 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 12, the OIS 28, the image acquisition device 32 could be implemented as a virtual machine. Given the processing power, memory, and computational capability available, the entire radiotherapy system 10 could be implemented as a virtual machine.

Figure 2:
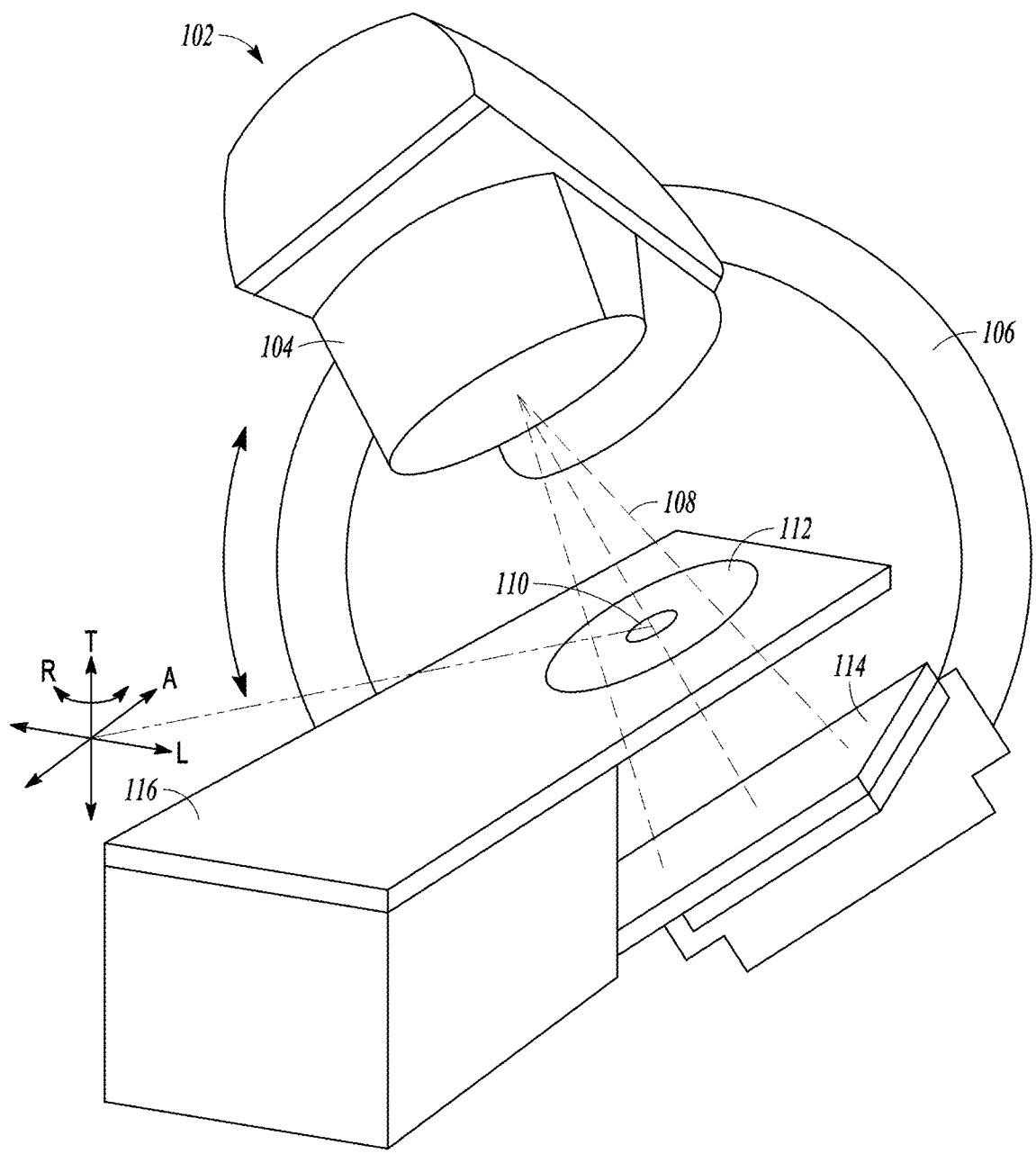
FIG. 2 illustrates an exemplary radiation therapy system that can include radiation therapy output configured to provide a therapy beam.

FIG. 2 illustrates an exemplary radiation therapy device 102 may include a radiation source, such as an X-ray source or a linear accelerator, a multi-leaf collimator (not shown), a couch 116, an imaging detector 114, and a radiation therapy output 104. The radiation therapy device 102 may be configured to emit a radiation beam 108 to provide therapy to a patient. The radiation therapy output 104 can include one or more attenuators or collimators, such as a multi-leaf collimator (MLC) as described in the illustrative example of FIG. 5, below.

Referring back to FIG. 2, a patient can be positioned in a region 112, using a table or couch 116 to receive a radiation therapy dose according to a radiation therapy treatment plan. The radiation therapy output 104 can be mounted or attached to a gantry 106 or other mechanical support. One or more chassis motors (not shown) may rotate the gantry 106 and the radiation therapy output 104 around couch 116 when the couch 116 is inserted into the treatment area. In an embodiment, gantry 106 may be continuously rotatable around couch 116 when the couch 116 is inserted into the treatment area. In another embodiment, gantry 106 may rotate to a predetermined position when the couch 116 is inserted into the treatment area. For example, the gantry 106 can be configured to rotate the therapy output 104 around an axis ("A"). Both the couch 116 and the radiation therapy output 104 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 116 movements or rotations in order to properly position the patient in or out of the radiation beam 108 position according to a radiation therapy treatment plan. As both the couch 116 and the gantry 106 are independently moveable from one another in multiple degrees of freedom, which allows the patient to be positioned such that the radiation beam 108 precisely can target the tumor.

The coordinate system (including axes A, T, and L) shown in FIG. 2 can have an origin located at an isocenter 110. The isocenter can be defined as a location where the radiation therapy beam 108 intersects the origin of a coordinate axis, such as to deliver a prescribed radiation dose to a location on or within a patient. For example, the isocenter 110 can be defined as a location where the radiation therapy beam 108 intersects the patient for various rotational positions of the radiation therapy output 104 as positioned by the gantry 106 around the axis A.

Gantry 106 may also have an attached imaging detector 114. The imaging detector 114 preferably located opposite to the radiation source 104, and in an example, the imaging detector 114 can be located within a field of the therapy beam 108.

The imaging detector 114 can be mounted on the gantry 106 preferably opposite the radiation therapy output 104, such as to maintain alignment with the therapy beam 108. The imaging detector 114 rotating about the rotational axis as the gantry 106 rotates. In an embodiment, the imaging detector 114 can be a flat panel detector (e.g., a direct detector or a scintillator detector). In this manner, the imaging detector 114 can be used to monitor the therapy beam 108 or the imaging detector 114 can be used for imaging the patient's anatomy, such as portal imaging. The control circuitry of radiotherapy device 102 may be integrated within system 100 or remote from it.

In an illustrative example, one or more of the couch 116, the therapy output 104, or the gantry 106 can be automatically positioned, and the therapy output 104 can establish the therapy beam 108 according to a specified dose for a particular therapy delivery instance. A sequence of therapy deliveries can be specified according to a radiation therapy treatment plan, such as using one or more different orientations or locations of the gantry 106, couch 116, or therapy output 104. The therapy deliveries can occur sequentially, but can intersect in a desired therapy locus on or within the patient, such as at the isocenter 110. A prescribed cumulative dose of radiation therapy can thereby be delivered to the therapy locus while damage to tissue nearby the therapy locus is reduced or avoided.

Figure 3:
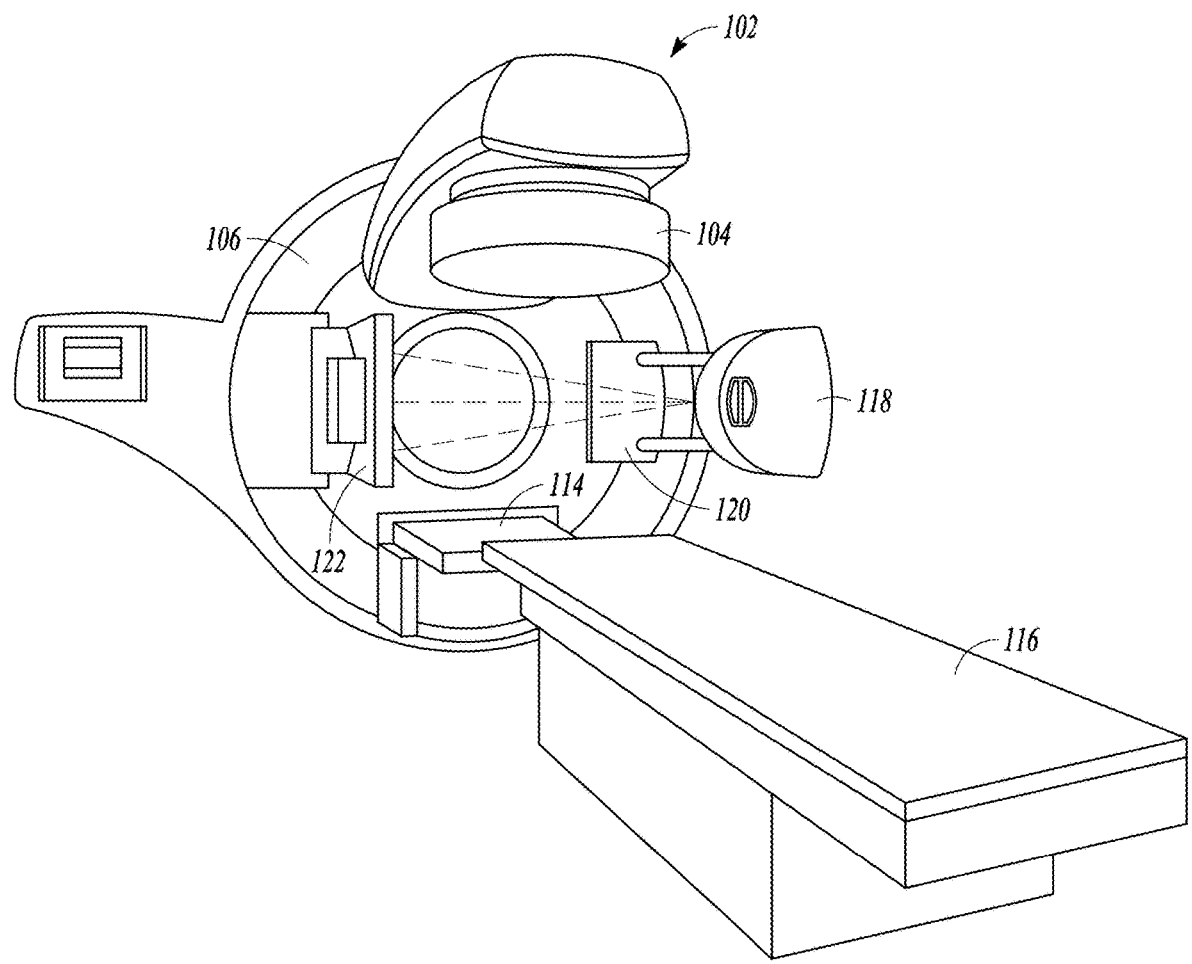
FIG. 3 illustrates an exemplary system including a combined radiation therapy system and an imaging system, such as a computed tomography (CT) imaging system.

FIG. 3 illustrates an exemplary radiation therapy device 102 that may include combining a linear accelerator and an imaging system, such as can include a computed tomography (CT) imaging system. The CT imaging system can include an imaging X-ray source 118, such as providing X-ray energy in a kiloelectron-Volt (keV) energy range. The imaging X-ray source 118 provide a fan-shaped and/or a conical beam 120 directed to an imaging detector 122, such as a flat panel detector. The radiation therapy system 102 can be similar to the system 102 described in relation to FIG. 2, such as including a radiation therapy output 104, a gantry 106, a platform 116, and another flat panel detector 114. The X-ray source 118 can provide a comparatively-lower-energy X-ray diagnostic beam, for imaging.

In the illustrative example of FIG. 3, the radiation therapy output 104 and the X-ray source 118 can be mounted on the same rotating gantry 106, rotationally-separated from each other by 90 degrees. In another example, two or more X-ray sources can be mounted along the circumference of the gantry 106, such as each having its own detector arrangement to provide multiple angles of diagnostic imaging concurrently. Similarly, multiple radiation therapy outputs 104 can be provided.

Figure 4A:
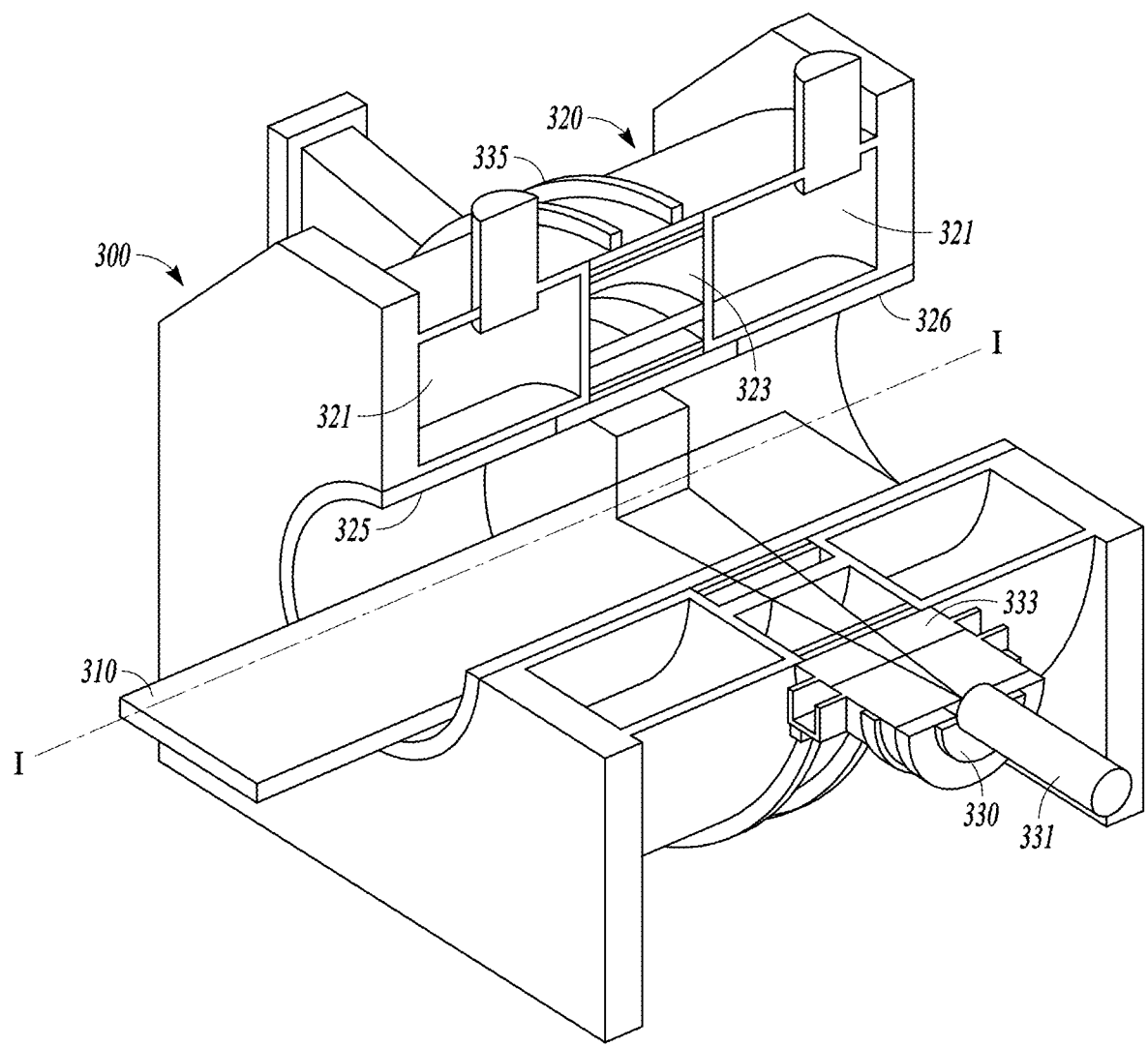
FIG. 4A illustrates a partially cut-away view of an exemplary system including a combined radiation therapy system and an imaging system, such as a nuclear magnetic resonance (MR) imaging system.
Figure 4B:
FIGS. 4B and 4C depict the differences between an exemplary MRI image and a corresponding CT image.
Figure 4C:
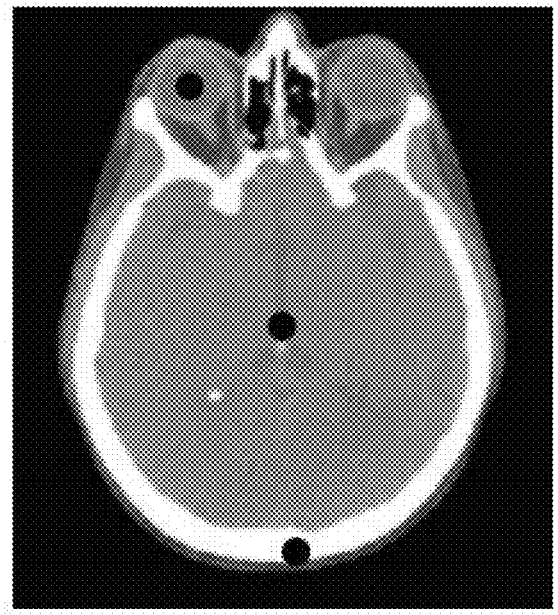

FIG. 4A depicts an exemplary radiation therapy system 300 that can include combining a radiation therapy device 102 and an imaging system, such as a nuclear magnetic resonance (MR) imaging system 130 (e.g., known in the art as a MR-Linac) consistent with the disclosed embodiments. As shown, system 300 may include a couch 310, an image acquisition device 320, and a radiation delivery device 330. System 300 delivers radiation therapy to a patient in accordance with a radiotherapy treatment plan. In some embodiments, image acquisition device 320 may correspond to image acquisition device 32 in FIG. 1 that may acquire origin images of a first modality (e.g., MRI image shown in FIG. 4B) or destination images of a second modality (e.g., CT image shown in FIG. 4C).

Couch 310 may support a patient (not shown) during a treatment session. In some implementations, couch 310 may move along a horizontal, translation axis (labelled "I"), such that couch 310 can move the patient resting on couch 310 into and/or out of system 300. Couch 310 may also rotate around a central vertical axis of rotation, transverse to the translation axis. To allow such movement or rotation, couch 310 may have motors (not shown) enabling the couch to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321, and may be displaced along that central axis. The displacement may create a gap, or window, between coils 325 and 326. In the embodiments where magnet 321 also includes a central window 323 between coils, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, or radiotherapy portal imaging device, etc. As would be recognized by one of ordinary skill in the art, the above description of image acquisition device 320 concerns certain embodiments and is not intended to be limiting.

Radiotherapy device 330 may include the source of radiation 331, such as an X-ray source or a linear accelerator, and a multi-leaf collimator (MLC) 333 (shown below in FIG. 5). Radiotherapy device 330 may be mounted on a chassis 335. One or more chassis motors (not shown) may rotate chassis 335 around couch 310 when couch 310 is inserted into the treatment area. In an embodiment, chassis 335 may be continuously rotatable around couch 310, when couch 310 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 310, image acquisition device 320, and radiotherapy device 330. The control circuitry of radiotherapy device 330 may be integrated within system 300 or remote from it.

During a radiotherapy treatment session, a patient may be positioned on couch 310. System 300 may then move couch 310 into the treatment area defined by magnetic coils 321, 325, 326, and chassis 335. Control circuitry may then control radiation source 331, MLC 333, and the chassis motor(s) to deliver radiation to the patient through the window between coils 325 and 326 according to a radiotherapy treatment plan.

FIG. 2, FIG. 3, and FIG. 4A illustrate generally illustrate examples of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

As discussed above, radiation therapy devices described by FIG. 2, FIG. 3, and FIG. 4A include a multi-leaf collimator for shaping, directing, or modulating an intensity of a radiation therapy beam to the specified target locus within the patient. FIG. 5 illustrates an exemplary multi-leaf collimator (MLC) 132 that includes leaves 132A through 132J that can be automatically positioned to define an aperture approximating a tumor 140 cross section or projection. The leaves 132A through 132J permit modulation of the radiation therapy beam. The leaves 132A through 132J can be made of a material specified to attenuate or block the radiation beam in regions other than the aperture, in accordance with the radiation treatment plan. For example, the leaves 132A through 132J can include metallic plates, such as comprising tungsten, with a long axis of the plates oriented parallel to a beam direction, and having ends oriented orthogonally to the beam direction (as shown in the plane of the illustration of FIG. 2). A "state" of the MLC 132 can be adjusted adaptively during a course of radiation therapy treatment, such as to establish a therapy beam that better approximates a shape or location of the tumor 140 or other target locus. This is in comparison to using a static collimator configuration or as compared to using an MLC 132 configuration determined exclusively using an "offline" therapy planning technique. A radiation therapy technique using the MLC 132 to produce a specified radiation dose distribution to a tumor or to specific areas within a tumor can be referred to as Intensity Modulated Radiation Therapy (IMRT).

Figure 6:
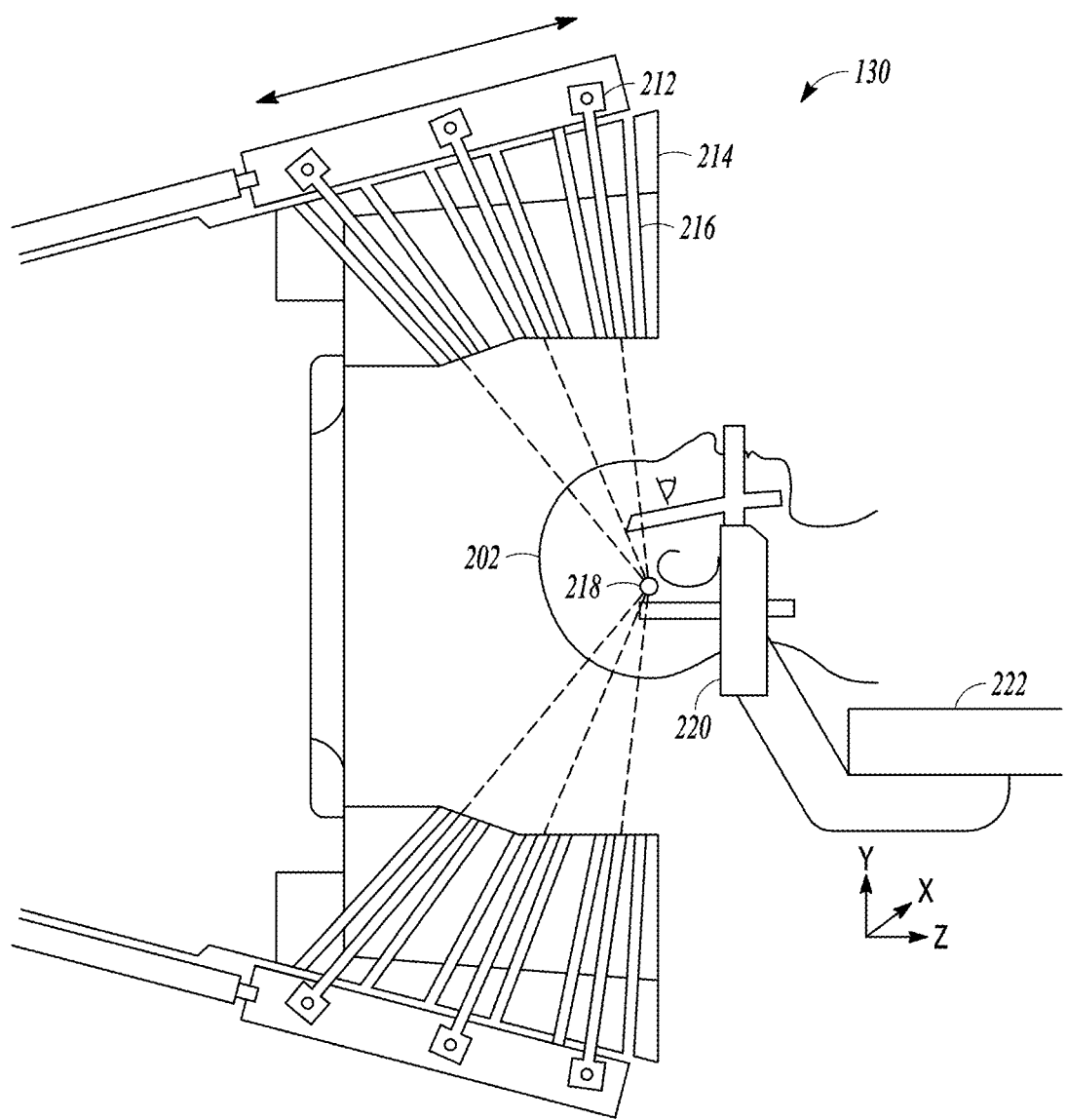
FIG. 6 illustrates an exemplary Gamma knife radiation therapy system.

FIG. 6 illustrates an example of another type of radiotherapy device 130 (e.g., a Leksell Gamma Knife), according to some embodiments of the present disclosure. As shown in FIG. 6, in a radiotherapy treatment session, a patient 202 may wear a coordinate frame 220 to keep stable the patient's body part (e.g., the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212. Radiation sources 212 may generate a plurality of radiation beams (e.g., beamlets) through beam channels 216. The plurality of radiation beams may be configured to focus on an isocenter 218 from different directions. While each individual radiation beam may have a relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

Figure 7:
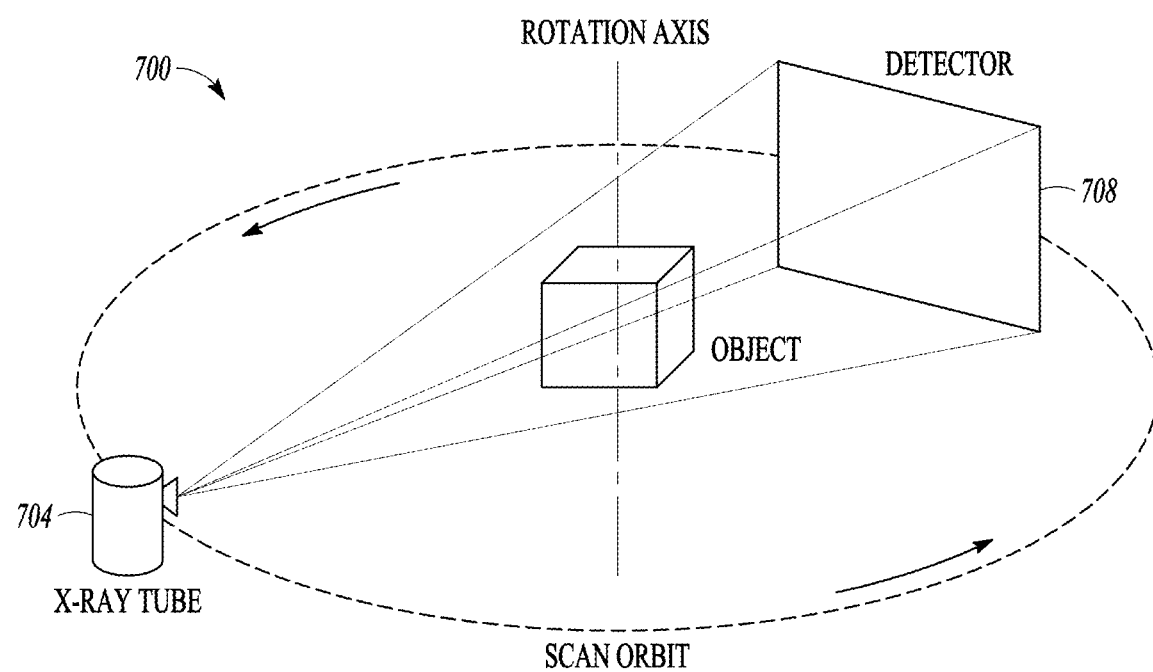
FIG. 7 illustrates an example of an X-ray cone beam computed tomography scanner.

FIG. 7 illustrates an example of an X-ray cone beam computed tomography scanner 700. The X-ray cone beam computed tomography scanner 700 can include an X-ray tube 704, and a detector 708. During operation, photons can be emitted from the X-ray tube 704 and can travel through a 3D object (e.g., a portion of a patient anatomy) before reaching the detector 708. The 3D object can absorb a portion of the emitted photons. The detector 708 can include a 2D flat plane that can convert received photons into corresponding electronic signals. The electronic signals can record the absorption strength along specific X-ray paths (straight-line paths), such as to form a 2D projection space image. To obtain 3D structural information of the 3D object, the 3D object can be rotated about a rotation axis or the X-ray tube 704 and detector 708 can be scanned in an orbit like trajectory to obtain 2D projection space images from different view angles. In an example, the 2D projection space images can be collected over a range of more than 200 degrees, such as can correspond to hundreds of 2D projection space images.

Image reconstruction algorithms can be employed to form a 3D image of the 3D object from the 2D projection space images collected by the X-ray cone beam computed tomography scanner 700. The reconstruction algorithms can include analytical and iterative reconstruction algorithms. In an example, analytical algorithms (such as Feldkamp or Feldkamp-modified algorithms) can be used to process the 2D projection space images collected by the scanner 700 to obtain 3D reconstructed images. In an example, the analytical algorithms can process the 2D projection space images in several seconds. However, the 3D reconstructed images can suffer from artifacts, such as those introduced by discrepancies between the collected 2D projection space images and mathematical assumptions associated with the analytical algorithms. Additionally, artifacts can arise from other sources, such as noise. In an example, iterative algorithms can be used to process the 2D projection space images collected by the scanner 700 to obtain 3D reconstructed images. The iterative algorithms can suppress some, but not all types of artifacts associated with analytical algorithms and can obtain better quality images than analytical algorithms, but the iterative algorithms can take a much longer time than the analytical algorithms, even with advanced GPU technology. Neither analytical, nor iterative algorithms are effective for all types of artifacts. Artifacts in the images can include any one or more of noise, scatter, extinction artifacts, beam hardening artifacts, exponential edge gradient effects, aliasing effects, ring artifacts, motion artifacts, or misalignment effects.

Noise artifacts can include additive noise from round-off errors or electrical noise. Noise artifacts can also include photon-count noise that can follow a Poisson distribution. CBCT machines can be operated at currents of milliamperes, which can be approximately one order of magnitude below that of CT machines, and thus signal-to-noise in CBCT images can be lower than in CT images. Scattering artifacts can be caused by photons scattered by an object that deviate from travel along a straight-line path. In certain reconstruction algorithms where photons can be assumed to be travelling in straight-line paths, artifacts can be introduced because of scattering. Scattering artifacts can include inhomogeneous darkening in CBCT 2D/3D images. Extinction artifacts can be present where an object contains strongly absorbing material and the photons cannot penetrate the object, leading to a signal on a detector that is very weak or zero. Absorption information can be lost where the signal on the detector is very weak or zero. Extinction artifacts in 2D CBCT projection space images can cause artifacts in reconstructed CBCT 2D/3D images, such as strong bright streak-like artifacts. Beam hardening artifacts can occur where a polychromatic x-ray beam is used to form the 2D CBCT projection space images. In a polychromatic x-ray beam, low energy x-rays can be preferentially absorbed by tissue in a patient, such as can lead to a relative increase in the ratio of high energy x-rays to low energy x-rays. The relative increase in the ratio can lead to artifacts in reconstructed CBCT 2D/3D images. Exponential edge gradient effects (EEGE) can occur at sharp edges with high contrast to neighboring structures. The EEGE can be caused by averaging a measured intensity over a finite beam width, whereas the algorithms for reconstruction assume a zero beam width. The EEGE can provide for a reduced computed density value and can cause streaks tangent to long straight edges in a direction of projection. Aliasing artifacts can occur when an image sampling frequency (pixels per unit area) is less than twice the value of the spatial frequency being sampled. Aliasing artifacts can also occur as a result of a diverging cone beam, such as that used in collecting CBCT projection space images. Ring artifacts can be caused by defects or uncalibrated detector elements. Ring artifacts can appear as concentric rings centered about an axis of rotation. Motion artifacts and misalignment effects can be caused by a misalignment of any one of a source, object, and detector during collection of the CBCT images.

Figure 8A:
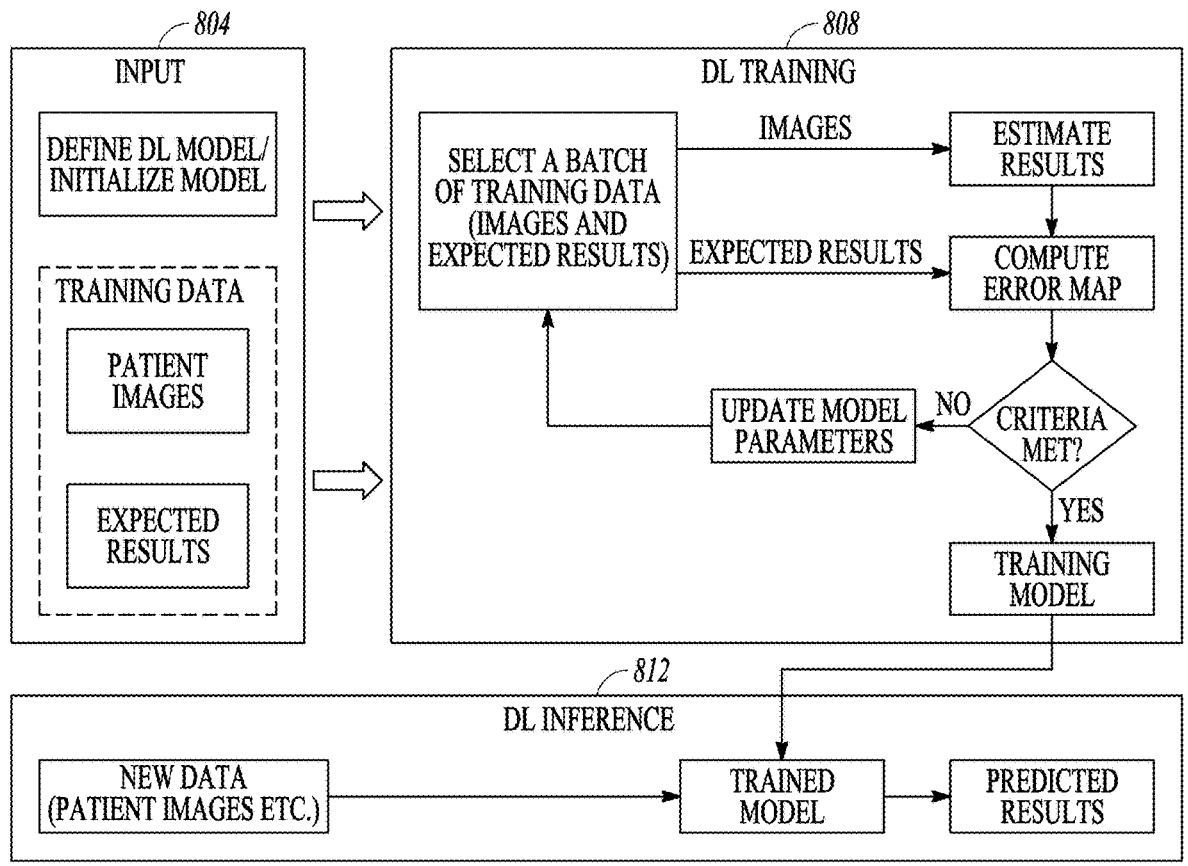
FIG. 8A illustrates an exemplary flow diagram for deep learning.

FIG. 8A illustrates an exemplary flow diagram for deep learning. Inputs 804 can include a defined deep learning model having an initial set of values, patient images, and expected results. In an example, the deep learning model can include a deep convolutional neural network. In an example, the patient images can include medical images, such as CBCT images. In an example, the medical images can be contaminated with artifacts and the expected results can include artifact reduced versions of the medical images. During a training of deep learning model 808, a batch of training data can be selected from the patient images and expected results. The deep learning model can be applied to the patient images to provide estimated results, which can then be compared to the expected results, such as to provide an error map. The error map can provide a measure of the differences between the estimated results and the expected results. The error map can be compared to predetermined criteria, such as can be provided by a user. If the error map does not satisfy the predetermined criteria, then model parameters of the deep learning model can be updated based on the error map and another batch of training data can be selected from the patient images and expected results and the deep learning model can be further trained. If the error map satisfies the predetermined criteria, then the training can be ended and the trained model can then be used during a deep learning inference stage 812 to remove artifacts from patient images different from the training data. The trained model can receive new patient images and provide predicted results (e.g., patient images having reduced artifacts).

Figure 8B:
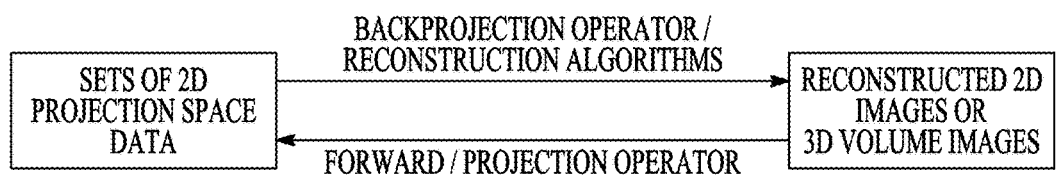
FIG. 8B illustrates an example of the relationship between projection space and image space.

FIG. 8B illustrates an example of the relationship between projection space and image space. In the example, sets of 2D projection space images, such as those that can be collected using the CBCT scanner 700 can be converted to reconstructed 3D volume images or reconstructed 2D images by using a backprojection operator or reconstruction algorithms (e.g. analytical or iterative). The reconstructed 3D volume images can then be converted back to sets of 2D projection space images by using a forward projection operator.

Figure 9A:
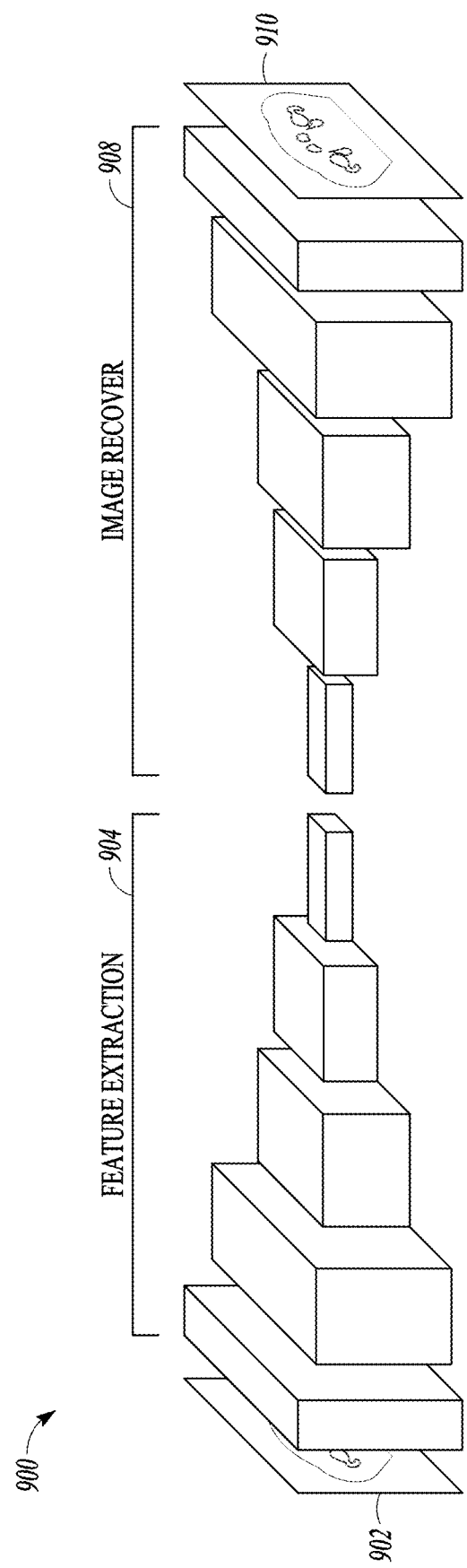
FIG. 9A illustrates an example of a deep convolutional neural network.

FIG. 9A illustrates an example of a deep convolutional neural network (DCNN) 900 for reducing artifacts in 2D CBCT projection space images in a projection space approach. In an example, the DCNN 900 can be a DCNN for regression. The DCNN 900 can be stored in a memory, such as the memory device 16 of image processing device 12. The DCNN 900 can include feature extraction layers 904 and image recovery layers 908. The feature extraction layers 904 and the image recovery layers 908 can include any one or more of convolution layers, pooling/sub-sampling layers, deconvolution layers, unpooling/upsampling layers, activation layers, normalization layers, copy layers, or crop layers.

The DCNN can receive 2D CBCT projection space images at an input 902, such as those collected with CBCT scanner 700. The feature extraction layers 904 can build a hierarchical feature extraction paradigm that extracts desired features at different scales and different complexity levels, where each of the extraction layers 904 receives as its input the latent representation of the preceding layer. The image recovery layers 908 can gradually recover and/or reconstruct artifact reduced 2D CBCT projection space images from coarse resolution to fine, until a desired 2D CBCT projection space image resolution or image size is achieved. In an example, the DCNN 900 can be trained as a whole (e.g., parameters of the feature extraction layers 904 and the image recovery layers 908 can be updated together during each iteration of a training model). In an example, the parameters of the feature extraction layer 908 and the parameters of the image recovery layers 908 can be updated separately. In an example, the parameters of the feature extraction layers 904 or the image recovery layers 908 can be initialized from weights from a pre-training model, such as a VGG image classification model. The other of the parameters of the feature extraction layers 904 or the image recovery layers 908 can be updated during each iteration of a training model.

Figure 9B:
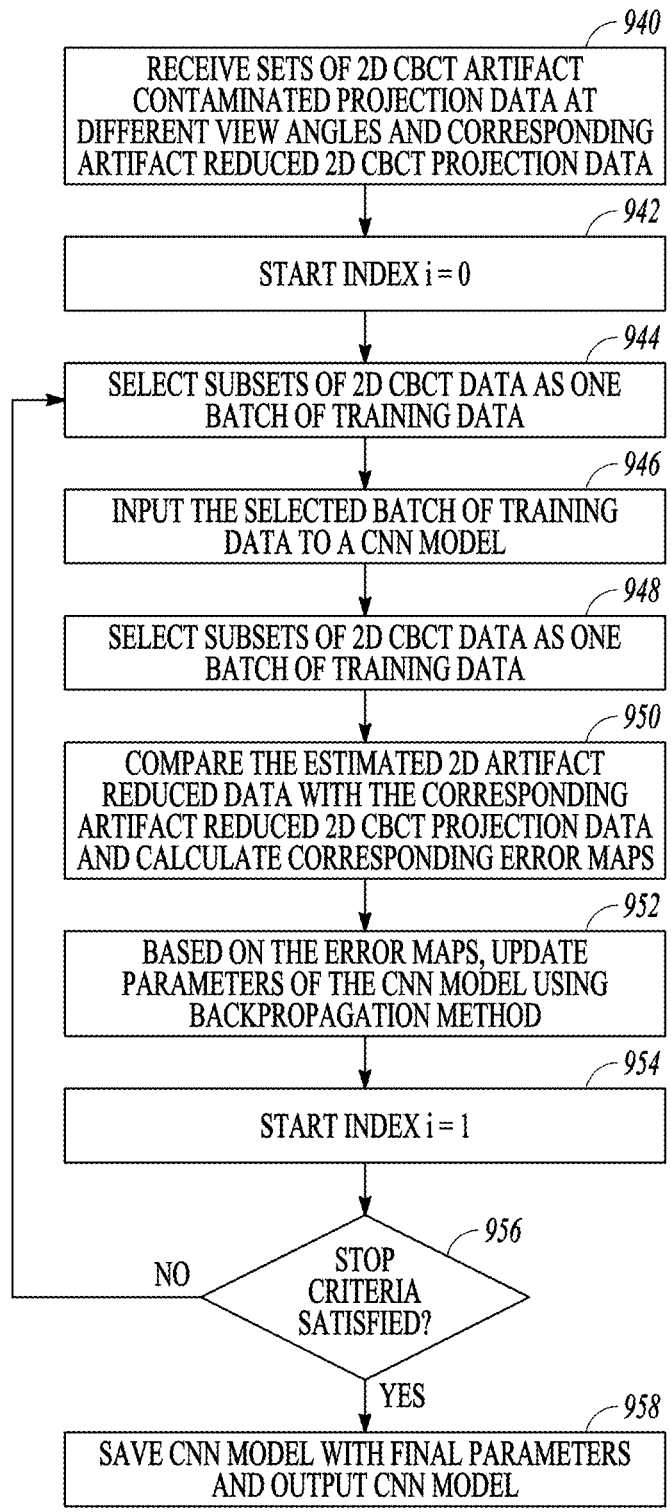
FIG. 9B illustrates an example of a method for training a DCNN.

FIG. 9B illustrates an example of a method for training a DCNN, such as DCNN 900 for reducing artifacts in 2D CBCT artifact contaminated projection space images in a projection space approach. The DCNN can receive sets of 2D CBCT projection space images contaminated with artifacts (step 940). The DCNN can also receive corresponding artifact reduced 2D CBCT projection space images. The received sets of 2D CBCT projection space images contaminated with artifacts and corresponding artifact reduced 2D CBCT projection space images can be collected from a group of patients (e.g., from each patient in a group of patients). In an example, the corresponding artifact reduced 2D CBCT projection space images can be free of artifacts or nearly free of artifacts. The corresponding artifact reduced 2D CBCT projection space images can be prepared offline by existing traditional methods (e.g. analytical or iterative algorithms), which can be very time consuming and complicated, and may not be suitable for real time or near real time applications. The sets of 2D CBCT artifact contaminated projection space images can include images at different view angles. In an example corresponding to a one-to-one training of the DCNN, the DCNN can receive a plurality of pairs of 2D CBCT projection space images from each patient in a group of patients, wherein each individual pair of 2D CBCT projection space images includes an artifact contaminated 2D CBCT projection space image and a corresponding artifact reduced 2D CBCT projection space image. In an example corresponding to a many-to-one training of the DCNN, the DCNN can receive a plurality of view-adjacent, artifact contaminated 2D CBCT projection space images and a corresponding artifact reduced 2D CBCT projection space image from each patient in a group of patients. In an example corresponding to a many-to-many training of the DCNN, the DCNN can receive an artifact contaminated 3D CBCT projection volume and a corresponding artifact reduced 3D CBCT projection volume for each patient in a group of patients. An iteration index can be set to an initial value of zero (step 942). A batch of training data can be formed from a subset of the 2D CBCT projection space images (step 944). The batch of training data can include 2D CBCT projection space images contaminated with artifacts such as noise, scatter, extinction artifacts, beam hardening artifacts, exponential edge gradient effects, aliasing effects, ring artifacts, motion artifacts, or misalignment effects. The batch of training data can also include corresponding artifact reduced 2D CBCT projection space images. The batch of training data can be provided to the DCNN (step 946). The DCNN can provide an output set of 2D CBCT projection space images based on current parameters of the DCNN (step 948). A comparison can be made between the output set of 2D CBCT projection space images and the corresponding artifact reduced 2D CBCT projection space images. In an example corresponding to a one-to-one training of the DCNN, each artifact contaminated 2D CBCT projection space image processed by the DCNN can be compared to a corresponding artifact reduced 2D CBCT projection space image. In an example corresponding to a many-to-one training of the DCNN, a predetermined (e.g., a central one) one of each plurality of view-adjacent contaminated 2D CBCT projection space images processed by the DCNN can be compared to a corresponding artifact reduced 2D CBCT projection space image. In an example corresponding to a many-to-many training of the DCNN, each artifact contaminated 3D CBCT projection volume processed by the DCNN can be compared to a corresponding artifact reduced 3D CBCT projection volume. Corresponding error maps can be determined from the comparison (step 950). Parameters of the DCNN can then be updated based on the corresponding error maps, such as by using backpropagation (step 952). After updating the parameters of the DCNN, the iteration index can be incremented by a value of one (step 954). The iteration index can correspond to a number of times that the parameters of the DCNN have been updated. Stopping criteria can be computed, and if the stopping criteria are satisfied, then the DCNN model can be saved in a memory, such as the memory device 16 of image processing device 12 and the training can be halted (step 958). If the stopping criteria are not satisfied, then the training can continue at step 944. In an example, the stopping criteria can include a value of the iteration index (e.g., the stopping criteria can include whether the iteration index is greater than or equal to a predetermined maximum number of iterations). In an example, the stopping criteria can also include an accuracy of the output set of 2D CBCT projection space images (e.g. the stopping criteria can include whether the difference between the output set of 2D CBCT projection space images and the artifact reduced 2D CBCT projection space images is smaller than a predetermined threshold).

Figure 9C:
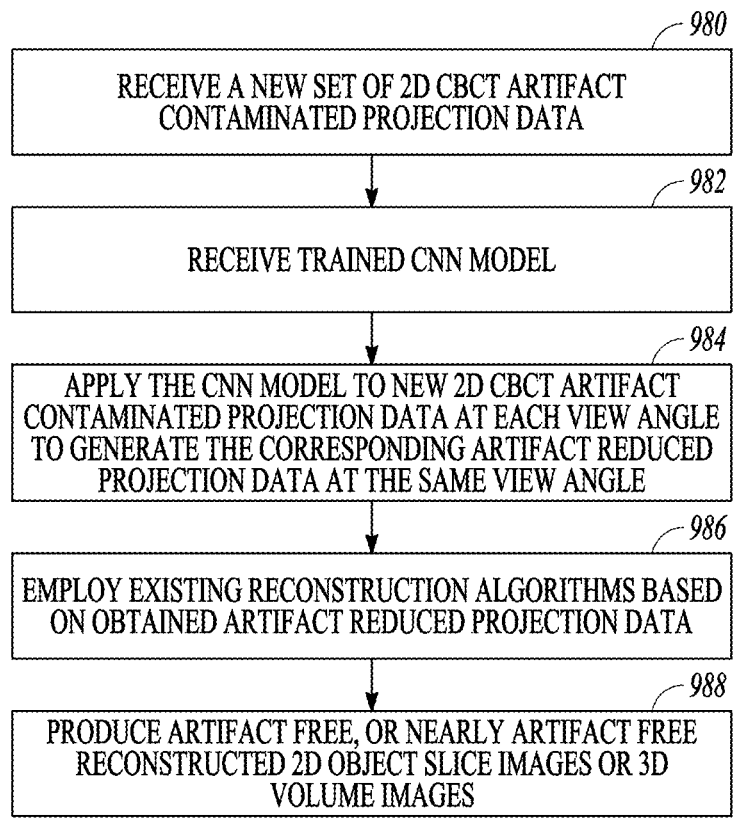
FIG. 9C illustrates an example of a method for generating artifact reduced, reconstructed 3D images using a trained DCNN.

FIG. 9C illustrates a method for generating artifact reduced, reconstructed 3D images using a trained DCNN, such as a DCNN that can be trained according to the method described above with respect to FIG. 9B. The DCNN can reduce artifacts such as noise, scatter, extinction artifacts, beam hardening artifacts, exponential edge gradient effects, aliasing effects, ring artifacts, motion artifacts, or misalignment effects. Sets of artifact contaminated 2D CBCT projection space images can be received for a plurality of viewing angles (step 980). A trained DCNN model can be received from a network, such as the network 20, or from a memory, such as the memory device 16 of image processing device 12 (step 982). The trained DCNN can be used to reduce artifacts (e.g., scatter artifacts or ring artifacts) in the received artifact contaminated 2D CBCT projection space images (step 984). In an example corresponding to a one-to-one training of the DCNN, one artifact reduced 2D CBCT projection space image can be provided by the DCNN for each artifact contaminated 2D CBCT projection space image received. In an example corresponding to a many-to-one training of the DCNN, one artifact reduced 2D CBCT projection space image can be provided by the DCNN for each plurality of view-adjacent artifact contaminated 2D CBCT images received. A provided one artifact reduced 2D CBCT projection space image can correspond to a central one of the corresponding plurality of received view-adjacent artifact contaminated 2D CBCT projection space images. In an example corresponding to a many-to-many training of the DCNN, one artifact reduced 3D CBCT projection volume can be provided by the DCNN for each artifact contaminated 3D CBCT projection volume received. The artifact reduced 2D CBCT projection space images can have increased compatibility with mathematical assumptions of reconstruction algorithms. Reconstruction algorithms can then be used to transform the artifact reduced 2D CBCT projection space images (step 986), such as to provide artifact reduced reconstructed 2D images or 3D volume images (step 988). In an example, the trained DCNN can generate artifact reduced, reconstructed 3D images for online applications, in real time, or near real time (e.g. the trained DCNN can generate 15-20 reconstructed clinically sized 2D images per second). In an example, the trained DCNN can remove or significantly reduce artifacts due to scattering in 2D CBCT projection space images and the reconstructed 2D images or 3D volume images can be free of or nearly free of scattering artifacts.

Figure 10A:
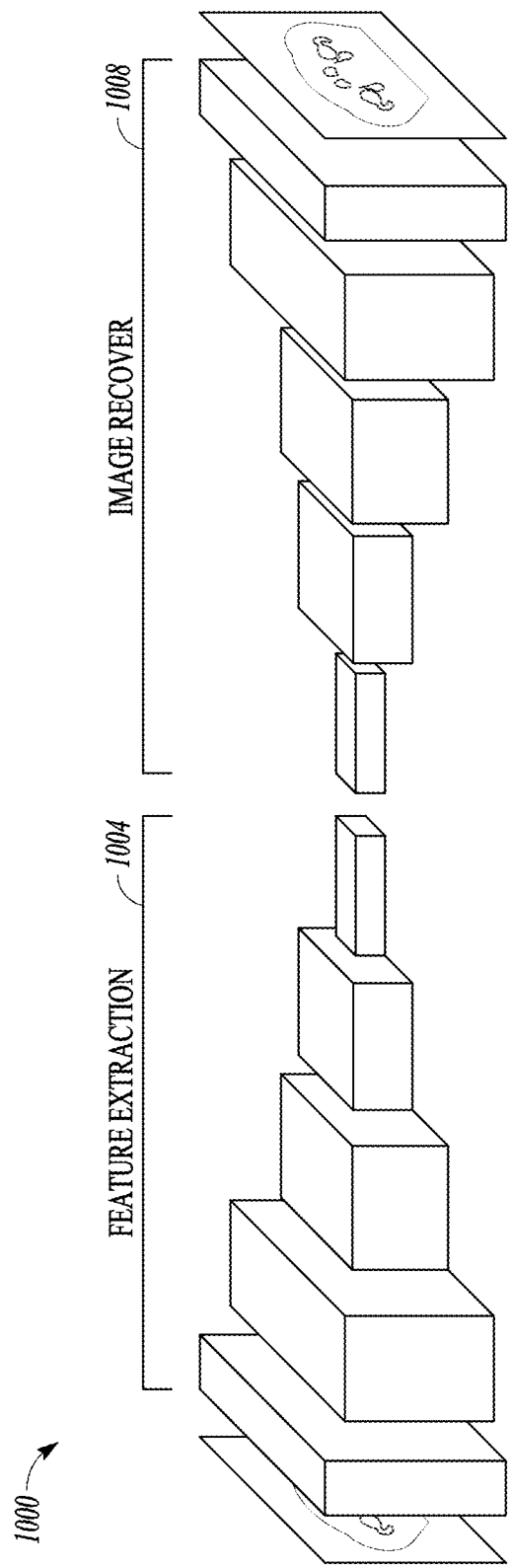
FIG. 10A illustrates an example of a deep convolutional neural network.

FIG. 10A illustrates an example of a deep convolutional neural network (DCNN) 1000 for reducing artifacts in 2D CBCT images in an image space approach. In an example, the DCNN 1000 can be a DCNN for regression. The DCNN 1000 can be stored in a memory, such as the memory device 16 of image processing device 12. The DCNN 1000 can include feature extraction layers 1004 and image recovery layers 1008. The feature extraction layers 1004 and the image recovery layers 1008 can include any one or more of convolution layers, pooling/sub-sampling layers, deconvolution layers, unpooling/upsampling layers, activation layers, normalization layers, copy layers, or crop layers.

Figure 10B:
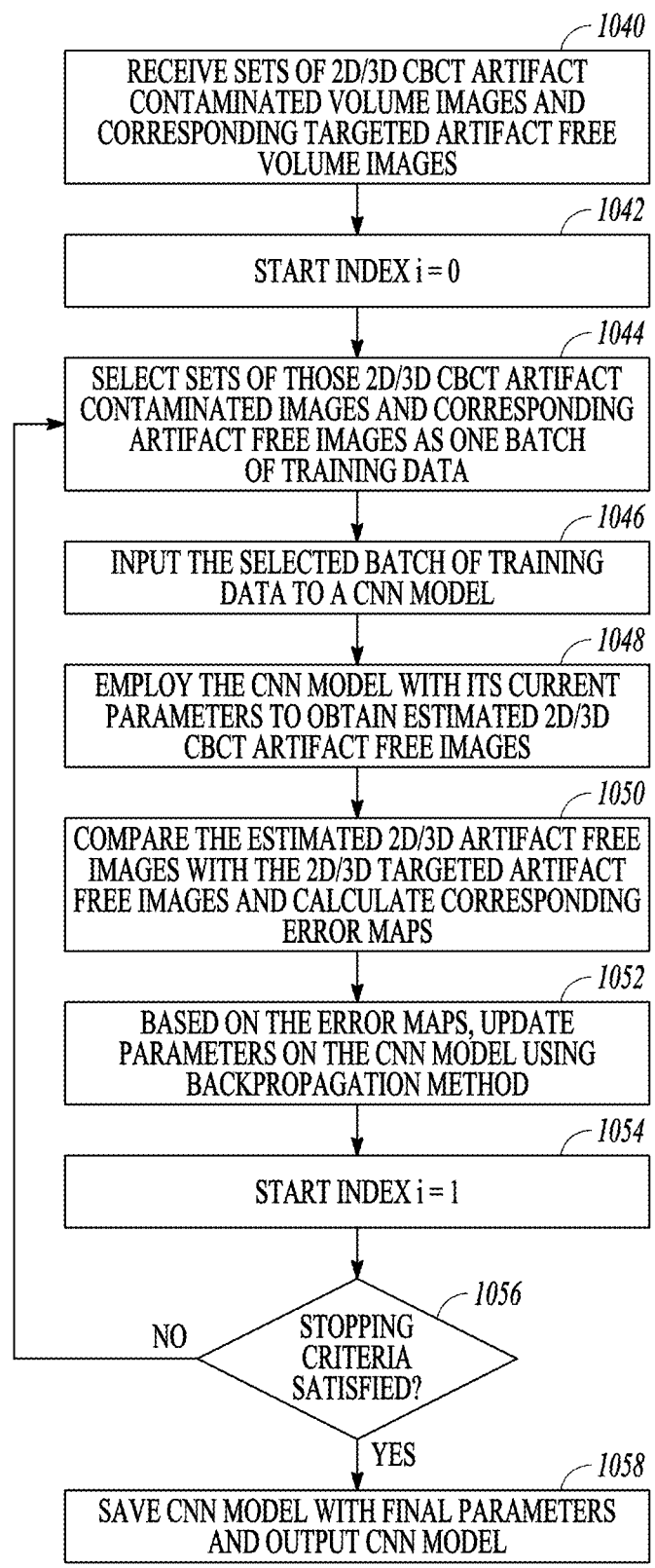
FIG. 10B illustrates an example of a method for training a DCNN.

FIG. 10B illustrates a method for training a DCNN, such as DCNN 1000 for reducing artifacts in 3D CBCT volume images in an image space approach. The DCNN can receive sets of 3D CBCT volume images contaminated with artifacts (step 1040). The DCNN can also receive corresponding artifact reduced 3D CBCT volume images. The received sets of 3D CBCT volume images contaminated with artifacts and corresponding artifact reduced 3D CBCT volume images can be collected from a group of patients (e.g., from each patient in a group of patients). In an example, the artifact reduced 3D CBCT volume images can be provided by using analytical algorithms or iterative algorithms to reduce artifacts in the artifact contaminated 3D CBCT volume images. In an example, the artifact reduced 3D CBCT volume images can be registered CT images. The corresponding artifact reduced 3D CBCT volume images can be prepared offline by methods (e.g., by CT imaging or by using algorithms) that may not be suitable for real time or near real time applications. In an example, the artifact contaminated 3D CBCT volume images can include a 3D CBCT volume image having scattering artifacts, and the corresponding artifact reduced 3D CBCT volume images can include a corresponding 3D CBCT volume image having reduced scattering artifacts. In an example, the artifact contaminated 3D CBCT volume images can include a 3D CBCT volume image having ring artifacts, and the corresponding artifact reduced 3D CBCT volume images can include a corresponding 3D CBCT volume image having reduced ring artifacts. In an example, the corresponding artifact reduced 3D CBCT volume images can be free of artifacts or nearly free of artifacts. In an example corresponding to a one-to-one training of the DCNN, the DCNN can receive a plurality of pairs of 2D images from each patient in a group of patients, wherein each individual pair of 2D images includes an artifact contaminated 2D CBCT image and a corresponding artifact reduced 2D image. The artifact reduced 2D image can include a registered CT image. In an example corresponding to a many-to-one training of the DCNN, the DCNN can receive a plurality of adjacent, artifact contaminated 2D CBCT images and a corresponding artifact reduced 2D CBCT image from each patient in a group of patients. The artifact reduced 2D image can include a registered CT image. In an example corresponding to a many-to-many training of the DCNN, the DCNN can receive an artifact contaminated 3D CBCT image volume and a corresponding artifact reduced 3D image volume for each patient in a group of patients. The artifact reduced 3D image volume can include a registered CT image. An iteration index can be set to an initial value of zero (step 1042). Sets of artifact contaminated 3D CBCT volume images and corresponding 3D artifact reduced CBCT or registered CT images can be selected to form a batch of training data (step 1044). The artifact contaminated 3D CBCT volume images include 3D CBCT volume images contaminated with artifacts such as noise, scatter, extinction artifacts, beam hardening artifacts, exponential edge gradient effects, aliasing effects, ring artifacts, motion artifacts, or misalignment effects. The batch of training data can be provided to the DCNN (step 1046). The DCNN can provide an output set of 3D CBCT volume images based on current parameters of the DCNN (step 1048). A comparison can be made between the output set of 3D CBCT volume images and corresponding artifact reduced 3D CBCT volume images. In an example corresponding to a one-to-one training of the DCNN, each artifact contaminated 2D CBCT image processed by the DCNN can be compared to a corresponding artifact reduced 2D image. The artifact reduced 2D image can include a registered 2D CT image. In an example corresponding to a many-to-one training of the DCNN, a predetermined (e.g., a central one) one of each plurality of adjacent artifact-contaminated 2D CBCT images processed by the DCNN can be compared to a corresponding artifact reduced 2D image. The artifact reduced 2D image can include a registered 2D CT image. In an example corresponding to a many-to-many training of the DCNN, each artifact contaminated 3D CBCT image volume processed by the DCNN can be compared to a corresponding artifact reduced 3D image volume. The artifact reduced 3D image volume can include a registered 3D CT image. Corresponding error maps can be determined from the comparison (step 1050). Parameters of the DCNN can then be updated based on the corresponding error maps, such as by using backpropagation (step 1052). After updating the parameters of the DCNN, the iteration index can be incremented by a value of one (step 1054). The iteration index can correspond to a number of times that the parameters of the DCNN have been updated. Stopping criteria can be computed, and if the stopping criteria are satisfied, then the DCNN model can be saved in a memory, such as the memory device 16 of image processing device 12 and the training can be halted (step 1058). If the stopping criteria are not satisfied, then the training can continue at step 1044. In an example, the stopping criteria can include a value of the iteration index (e.g., the stopping criteria can include whether the iteration index is greater than or equal to a predetermined maximum number of iterations). In an example, the stopping criteria can also include an accuracy of the output set of 3D CBCT volume images (e.g. the stopping criteria can include whether the difference between the output set of 3D CBCT volume images and the artifact reduced 3D CBCT volume images is smaller than a predetermined threshold).

Figure 10C:
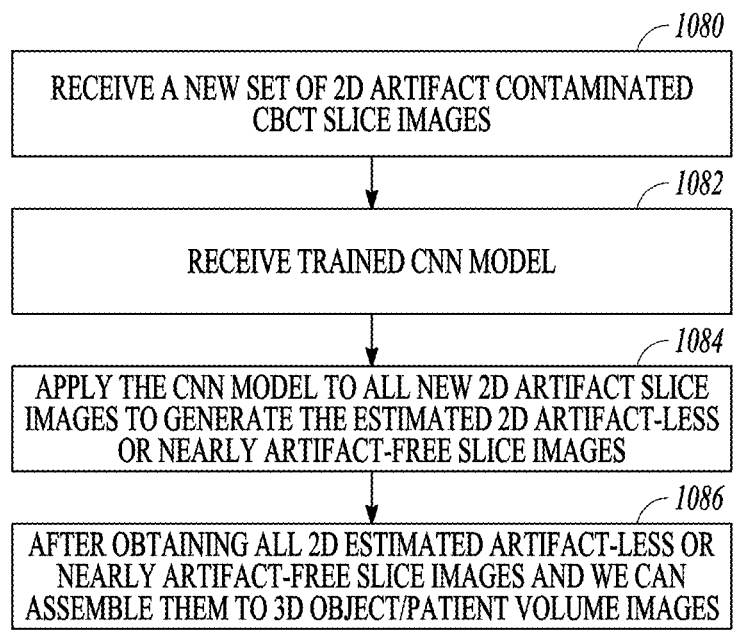
FIG. 10C illustrates an example of a method for generating artifact reduced, reconstructed 3D images using a trained DCNN.

FIG. 10C illustrates a method for generating artifact reduced, 3D volume images or 2D CBCT images using a trained DCNN, such as a DCNN that can be trained according to the method described above with respect to FIG. 10B. The DCNN can reduce artifacts such as noise, scatter, extinction artifacts, beam hardening artifacts, exponential edge gradient effects, aliasing effects, ring artifacts, motion artifacts, or misalignment effects. Sets of artifact contaminated 2D CBCT images can be received (step 1080). A trained DCNN model can be received from a network, such as the network 20, or from a memory, such as the memory device 16 of image processing device 12 (step 1082). The trained DCNN can be used to reduce artifacts in the received artifact contaminated 2D CBCT images (step 1084). In an example corresponding to a one-to-one training of the DCNN, one artifact reduced 2D CBCT image can be provided by the DCNN for each artifact contaminated 2D CBCT image received. In an example corresponding to a many-to-one training of the DCNN, one artifact reduced 2D CBCT image can be provided by the DCNN for each plurality of adjacent artifact contaminated 2D CBCT images received. A provided one artifact reduced 2D CBCT image can correspond to a central one of the corresponding plurality of received adjacent artifact contaminated 2D CBCT images. In an example corresponding to a many-to-many training of the DCNN, one artifact reduced 3D CBCT image volume can be provided by the DCNN for each artifact contaminated 3D CBCT image volume received. In an example, a first portion of the DCNN, such as the feature extraction portion 1004 can extract features identified as non-artifacts in artifact contaminated 2D CBCT images. A second portion of the DCNN, such as the image recovery portion 1008 can then reconstruct artifact reduced 2D CBCT images from the features extracted by the first portion of the DCNN. The artifact reduced 2D CBCT images can then be assembled to form artifact reduced 3D volume images (step 1086). In an example, the trained DCNN can generate artifact reduced, 3D volume images or 2D CBCT images for online applications, in real time, or near real time (e.g. the trained DCNN can generate 15-20 artifact reduced 2D CBCT images per second). In an example, the trained DCNN can remove or significantly reduce artifacts due to scattering and the 2D CBCT images or 3D volume images can be free of or nearly free of scattering artifacts, such as can lead to improved image contrast. In an example, the trained DCNN can remove or significantly reduce ring artifacts, such as can appear as ring shapes in artifact contaminated 2D or 3D CBCT images.

Figure 10D:
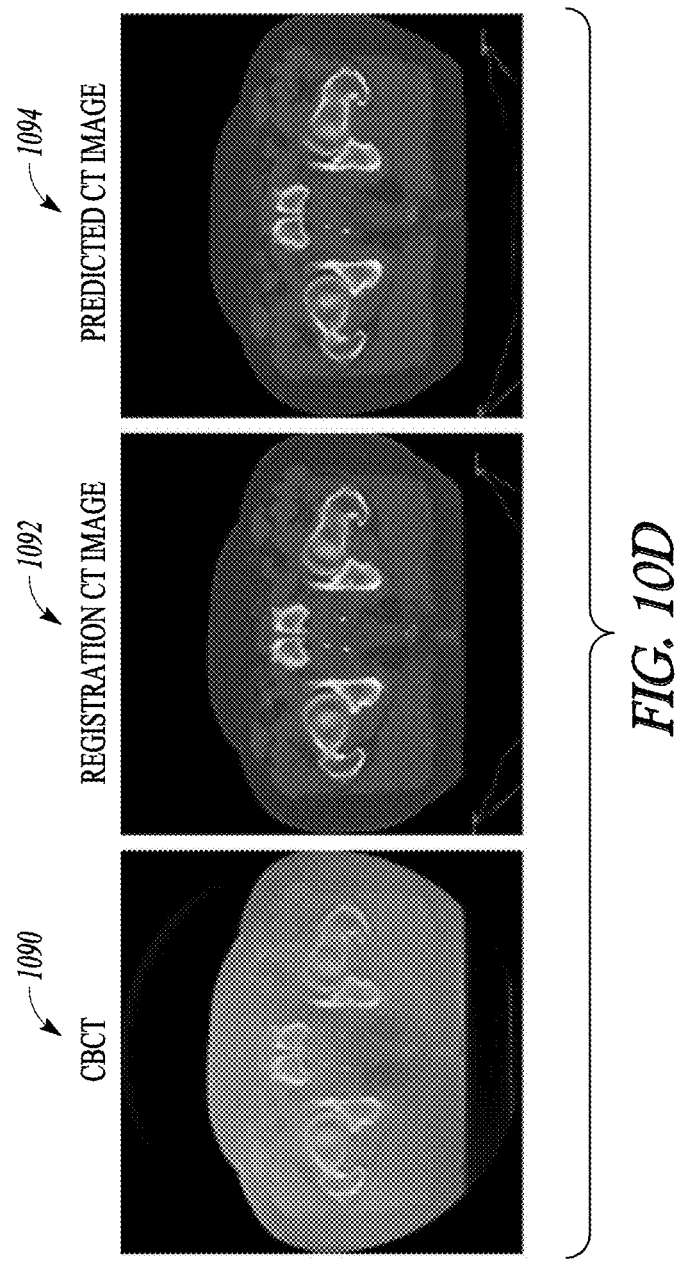
FIG. 10D illustrates an example of a 2D CBCT images.

FIG. 10D illustrates an example of a 2D CBCT image 1090 collected from a patient, a registered CT image 1092 collected from the patient, and an artifact reduced 2D CBCT image 1094, such as that provided by using a DCNN, such as the DCNN trained using the method described with respect to FIG. 10B. The 2D CBCT image 1090 can be contaminated with artifacts, the registered CT image 1092 is artifact free, or nearly artifact free, and the artifact reduced 2D CBCT image 1094 can closely match the registered CT image 1092 after processing by the DCNN.

Figure 11:
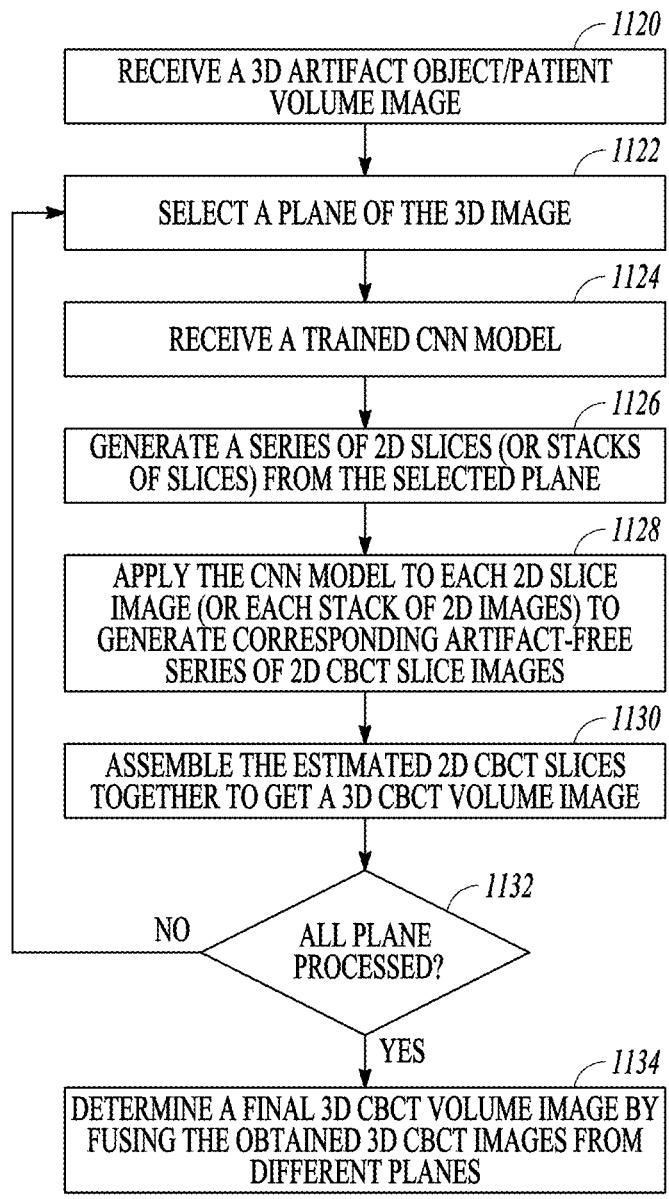
FIG. 11 illustrates an example of a method for generating artifact reduced 3D CBCT images.

FIG. 11 illustrates another embodiment for generating artifact reduced 3D CBCT images. A 3D CBCT volume image contaminated with artifacts can be received (step 1120). A plane of the 3D CBCT image can be selected (step 1122). A trained DCNN model can be received, such as that trained according to the method described with respect to FIG. 10B (step 1124). A series of 2D images can be generated from the selected plane (step 1126). The received DCNN model can be applied to each of the series of 2D images to generate corresponding artifact reduced 2D CBCT images (step 1128). The generated artifact reduced 2D CBCT images can then be assembled to form an artifact reduced 3D CBCT volume image (step 1130). If not all planes of the artifact contaminated 3D CBCT volume image have been processed, then another plane of the artifact contaminated 3D CBCT volume image can be selected at step 1122 before proceeding again with steps 1124-1130. If all planes of the artifact contaminated 3D CBCT volume image have been processed, then a final artifact reduced 3D CBCT image can be formed by fusing the artifact reduced 3D CBCT volume images corresponding to different selected planes. In an example, different selected planes of the artifact contaminated 3D CBCT image can be processed using different trained DCNN models.

Figure 12:
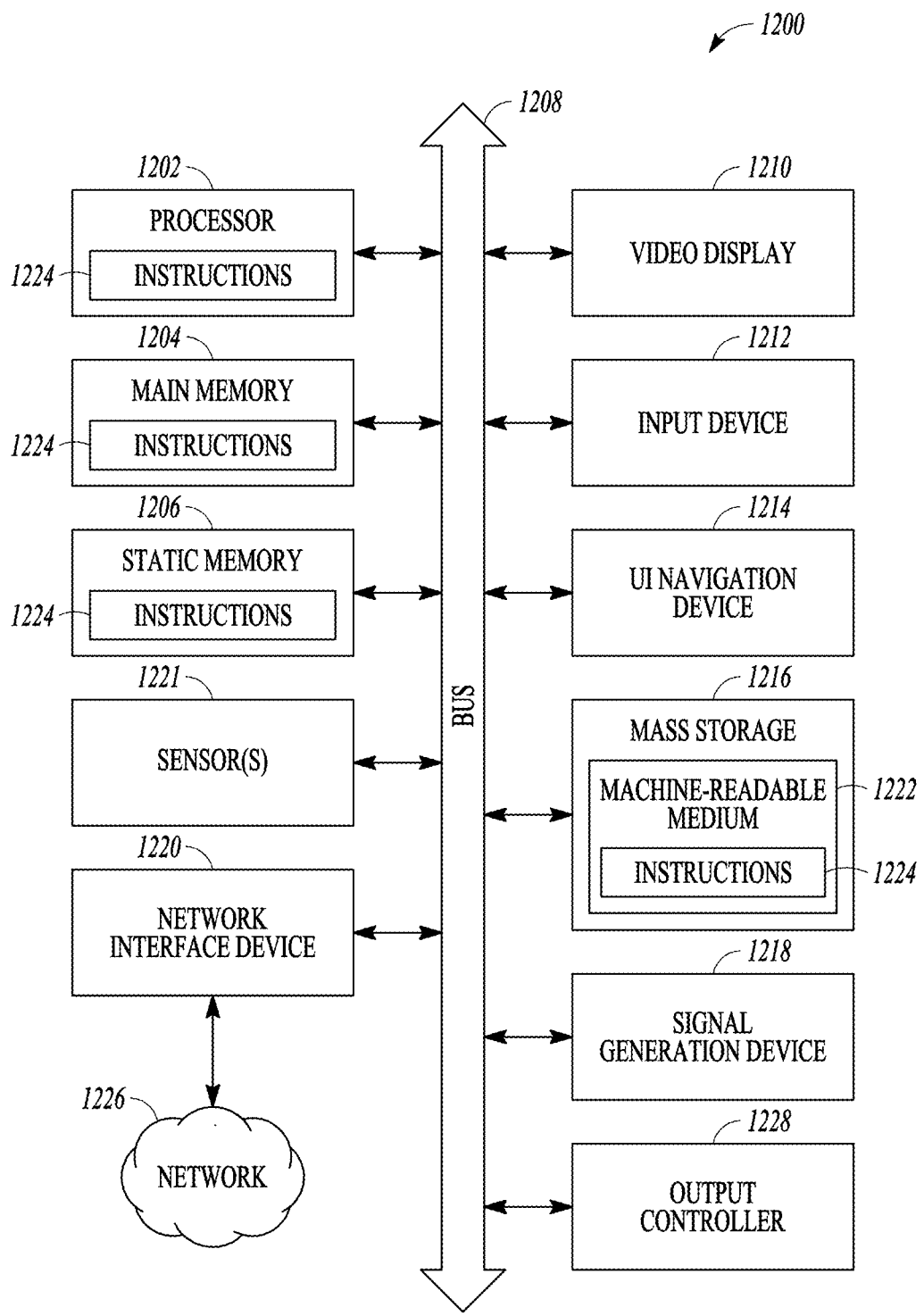
FIG. 12 illustrates an example of a block diagram of an embodiment of a machine on which one or more of the methods as discussed herein can be implemented.

FIG. 12 illustrates, by way of example, a block diagram of an embodiment of a machine 1200 on which one or more of the methods as discussed herein can be implemented. In one or more embodiments, one or more items of the image processing device 12 can be implemented by the machine 1200. In alternative embodiments, the machine 1200 operates as a standalone device or may be connected (e.g., networked) to other machines. In one or more embodiments, the image processing device 12 can include one or more of the items of the machine 1200. In a networked deployment, the machine 1200 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1200 includes processing circuitry 1202 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 1221 (e.g., a transducer that converts one form of energy (e.g., light, heat, electrical, mechanical, or other energy) to another form of energy), or the like, or a combination thereof), a main memory 1204 and a static memory 1206, which communicate with each other via a bus 1208. The machine 1200 (e.g., computer system) may further include a video display unit 1210 (e.g., a liquid crystal display (LCD) or a cathode ray tube (CRT)). The machine 1200 also includes an alphanumeric input device 1212 (e.g., a keyboard), a user interface (UI) navigation device 1214 (e.g., a mouse), a disk drive or mass storage unit 1216, a signal generation device 1218 (e.g., a speaker) and a network interface device 1220.

The disk drive unit 1216 includes a machine-readable medium 1222 on which is stored one or more sets of instructions and data structures (e.g., software) 1224 embodying or utilized by any one or more of the methodologies or functions described herein. The instructions 1224 may also reside, completely or at least partially, within the main memory 1204 and/or within the processor 1202 during execution thereof by the machine 1200, the main memory 1204 and the processor 1202 also constituting machine-readable media.

The machine 1200 as illustrated includes an output controller 1228. The output controller 1228 manages data flow to/from the machine 1200. The output controller 1228 is sometimes called a device controller, with software that directly interacts with the output controller 1228 being called a device driver.

While the machine-readable medium 1222 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 1224 may further be transmitted or received over a communications network 1226 using a transmission medium. The instructions 1224 may be transmitted using the network interface device 1220 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., Wi-Fi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

Embodiments of the invention may be implemented with computer-executable instructions. The computer-executable instructions (e.g., software code) may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CDROMS, magnetic-optical disks, removable optical disks (e.g., compact disks and digital video disks), flash memory devices, magnetic cassettes, memory cards or sticks (e.g., secure digital cards), random access memories (RAMS) (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an embodiment the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various embodiments of the invention, the method of creating a component or module can be implemented in software, hardware, or a combination thereof. The methods provided by various embodiments of the present invention, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general purpose computer selectively activated or reconfigured by a computer program stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A method for training a deep convolutional neural network to reduce one or more artifacts in at least one projection space image, the method comprising:
    obtaining a three-dimensional, artifact contaminated cone beam computed tomography (CBCT) projection volume, and a plurality of corresponding three-dimensional, artifact reduced CBCT projection volumes obtained from respective patients in a group of patients; and
    using images from the artifact contaminated CBCT projection volume and images from the corresponding artifact reduced, CBCT projection volumes obtained from the group of patients to train a deep convolutional neural network to reduce at least one artifact in at least one of the images in an evaluated CBCT projection volume.

2. The method of claim 1, wherein the obtaining of the images comprises collecting a plurality of pairs of projection space images from each patient in the group of patients,
wherein an individual pair of projection space images includes an artifact contaminated CBCT projection space image and a corresponding artifact reduced CBCT projection space image, and
wherein the using of the images to train the deep convolutional neural network comprises using the plurality of pairs of projection space images collected from each patient in the group of patients to train the deep convolutional neural network to reduce the at least one artifact in at least one of the images in the evaluated CBCT projection volume.

3. The method of claim 1, wherein the artifact contaminated CBCT projection volume includes a plurality of view-adjacent projection space images, and
wherein the three-dimensional, artifact reduced CBCT projection volumes respectively include a plurality of view-adjacent projection space images.

4. The method of claim 1, wherein the deep convolutional neural network is configured to receive the evaluated CBCT projection volume as an input and perform regression on the input.

5. The method of claim 1, wherein the trained deep convolutional neural network is configured to reduce the at least one artifact among a plurality of images in the evaluated CBCT projection volume, and
wherein the at least one artifact includes at least one of: a scattering artifact, a beam hardening artifact, a noise artifact, an extinction artifact, an exponential edge gradient artifact, an aliasing artifact, a ring artifact, a streaking artifact, or a motion artifact.

6. A method of using a deep convolutional neural network to reduce one or more artifacts in a projection space image obtained from a patient, the method comprising:
collecting a three-dimensional artifact contaminated cone beam computed tomography (CBCT) projection volume of a patient, the artifact contaminated CBCT volume including at least one projection space image; and
using a trained deep convolutional neural network to reduce at least one artifact in the at least one CBCT projection space image of the artifact contaminated CBCT volume, the deep convolutional neural network including a model trained by using a three-dimensional, artifact contaminated CBCT projection volume and a corresponding artifact reduced, CBCT projection volume collected from respective patients in a group of patients.

7. The method of claim 6, wherein the trained deep convolutional neural network reduces at least one artifact in a projection space image collected from the patient in near real-time, and
wherein the at least one artifact includes at least one of a scattering artifact, a beam hardening artifact, a noise artifact, an extinction artifact, an exponential edge gradient artifact, an aliasing artifact, a ring artifact, a streaking artifact, or a motion artifact.

8. The method of claim 6, wherein the collecting of the artifact contaminated CBCT volume comprises collecting a plurality of view-adjacent, artifact contaminated CBCT projection space images from the patient, and
wherein using the trained deep convolutional neural network comprises using the trained deep convolutional neural network to reduce the at least one artifact in the view-adjacent, artifact contaminated CBCT projection space images collected from the patient.

9. The method of claim 8, wherein the trained deep convolutional neural network uses at least one correlation between the plurality of view-adjacent, artifact contaminated CBCT projection space images collected from the patient to reduce the at least one artifact in a central one of the plurality of view-adjacent, artifact contaminated CBCT projection space images collected from the patient.

10. The method of claim 6, wherein the model is trained by using a collected plurality of pairs of projection space images from the respective patients in the group of patients, and
wherein an individual pair of projection space images used in training of the model includes an artifact contaminated CBCT projection space image and a corresponding artifact reduced CBCT projection space image.

11. A method for training a deep convolutional neural network to reduce one or more artifacts in a cone beam computed tomography (CBCT) anatomical image, the method comprising:
obtaining a plurality of CBCT anatomical images from an artifact contaminated CBCT anatomical volume, and a plurality of computed tomography (CT) anatomical images obtained from at least one corresponding artifact reduced CT anatomical volume for respective patients in a group of patients; and
using the plurality of CBCT anatomical images and the corresponding CT anatomical images to train a deep convolutional neural network to reduce at least one artifact in at least one evaluated CBCT anatomical image.

12. The method of claim 11, wherein the obtaining of the images comprises collecting a plurality of pairs of anatomical images from each patient in the group of patients, and
wherein an individual pair of anatomical images includes an artifact contaminated CBCT anatomical image and a corresponding artifact reduced CT anatomical image for a particular patient.

13. The method of claim 11, wherein the obtaining of the images comprises collecting a plurality of adjacent, artifact contaminated CBCT anatomical images, and an artifact reduced CT anatomical image corresponding to a central one of the plurality of adjacent, artifact contaminated CBCT anatomical images, for each patient in a group of patients, and
wherein the using of the images to train the deep convolutional neural network comprises using the collected images to train the deep convolutional neural network to reduce at least one artifact in at least a central one of an evaluated plurality of CBCT anatomical images.

14. The method of claim 11, wherein the using of the images to train the deep convolutional neural network comprises using the obtained images to train the deep convolutional neural network to remove at least one artifact in an evaluated CBCT anatomical volume, and
wherein the evaluated CBCT anatomical volume includes the at least one evaluated CBCT anatomical image.

15. The method of claim 11, wherein at least one of iterative algorithms, computer simulations, physical phantoms, or registered CT anatomical images are used to produce the plurality of CT anatomical images from the at least one corresponding artifact reduced CT anatomical volume for respective patients in a group of patients.

16. A method of using a deep convolutional neural network to reduce one or more artifacts in an anatomical image obtained of a patient, the method comprising:
    collecting at least one artifact contaminated cone beam computed tomography (CBCT) anatomical image produced from imaging of the patient; and
    using a trained deep convolutional neural network to reduce at least one artifact in the at least one CBCT anatomical image collected from the patient, the deep convolutional neural network including a model trained by using anatomical images from at least one artifact contaminated CBCT anatomical volume, and at least one corresponding artifact reduced computed tomography (CT) anatomical volume for respective patients in a group of patients.

17. The method of claim 16, wherein the trained deep convolutional neural network reduces at least one artifact in the CBCT anatomical image located within an artifact contaminated CBCT anatomical volume,
    wherein the artifact contaminated CBCT anatomical volume is collected from the patient in near real-time, and
    wherein the at least one artifact includes at least one of a scattering artifact, a beam hardening artifact, a noise artifact, an extinction artifact, an exponential edge gradient artifact, an aliasing artifact, a ring artifact, a streaking artifact, or a motion artifact.

18. The method of claim 16, wherein the collecting of the at least one artifact contaminated CBCT anatomical image comprises collecting a plurality of adjacent, artifact contaminated CBCT anatomical images, and
    wherein using the trained deep convolutional neural network comprises using the trained deep convolutional neural network to reduce the at least one artifact in a central one of the plurality of adjacent, artifact contaminated CBCT anatomical images collected from the patient, the deep convolutional neural network including a model trained by using a collected plurality of adjacent, artifact contaminated CBCT anatomical images, and an artifact reduced computed tomography anatomical image corresponding to the central one of the plurality of adjacent, artifact contaminated CBCT anatomical images for each patient in a group of patients.

19. The method of claim 16, wherein the deep convolutional neural network includes a model trained by using a collected at least one artifact contaminated CBCT anatomical volume, and at least one corresponding artifact reduced CT anatomical volume for each patient in a group of patients.

20. At least one non-transitory machine-readable storage medium comprising instructions, wherein the instructions, when executed by a processing circuitry of a computing device, cause the processing circuitry to perform operations to reduce one or more artifacts in an anatomical image obtained of a patient, the operations comprising:
    collecting a three-dimensional artifact contaminated cone beam computed tomography (CBCT) projection volume of a patient, the artifact contaminated CBCT volume including at least one projection space image; and
    using a trained deep convolutional neural network to reduce at least one artifact in the at least one CBCT projection space image of the artifact contaminated CBCT volume, the deep convolutional neural network including a model trained by using a three-dimensional, artifact contaminated CBCT projection volume and a corresponding artifact reduced, CBCT projection volume collected from respective patients in a group of patients.

21. The machine-readable storage medium of claim 20, wherein the trained deep convolutional neural network reduces at least one artifact in a projection space image collected from the patient in near real-time, and
    wherein the at least one artifact includes at least one of a scattering artifact, a beam hardening artifact, a noise artifact, an extinction artifact, an exponential edge gradient artifact, an aliasing artifact, a ring artifact, a streaking artifact, or a motion artifact.

22. At least one non-transitory machine-readable storage medium comprising instructions, wherein the instructions, when executed by processing circuitry of a computing device, cause the processing circuitry to perform operations to reduce one or more artifacts in an anatomical image obtained of a patient, the operations comprising:
    collecting at least one artifact contaminated cone beam computed tomography (CBCT) anatomical image produced from imaging of the patient; and
    using a trained deep convolutional neural network to reduce at least one artifact in the at least one CBCT anatomical image collected from the patient, the deep convolutional neural network including a model trained by using anatomical images from at least one artifact contaminated CBCT anatomical volume, and at least one corresponding artifact reduced computed tomography (CT) anatomical volume for respective patients in a group of patients.

23. The machine-readable storage medium of claim 22, wherein the trained deep convolutional neural network reduces at least one artifact in the CBCT anatomical image located within an artifact contaminated CBCT anatomical volume,
    wherein the artifact contaminated CBCT anatomical volume is collected from the patient in near real-time, and
    wherein the at least one artifact includes at least one of a scattering artifact, a beam hardening artifact, a noise artifact, an extinction artifact, an exponential edge gradient artifact, an aliasing artifact, a ring artifact, a streaking artifact, or a motion artifact.

* * * * *